(12) United States Patent
Kitano et al.

(10) Patent No.: US 9,137,122 B2
(45) Date of Patent: Sep. 15, 2015

(54) NETWORK MODEL INTEGRATION DEVICE, NETWORK MODEL INTEGRATION SYSTEM, NETWORK MODEL INTEGRATION METHOD, AND COMPUTER PROGRAM PRODUCT

(75) Inventors: Hiroaki Kitano, Okinawa (JP); Yukiko Matsuoka, Tokyo (JP); Samik Ghosh, Tokyo (JP)

(73) Assignees: OKINAWA INSTITUTE OF SCIENCE AND TECHNOLOGY GRADUATE UNIVERSITY, Kunigami-gun (JP); The Systems Biology Institute, Tokyo (JP)

( * ) Notice: Subject to any disclaimer, the term of this patent is extended or adjusted under 35 U.S.C. 154(b) by 346 days.

(21) Appl. No.: 13/876,283

(22) PCT Filed: Mar. 31, 2011

(86) PCT No.: PCT/JP2011/058323
§ 371 (c)(1),
(2), (4) Date: Mar. 27, 2013

(87) PCT Pub. No.: WO2012/042952
PCT Pub. Date: Apr. 5, 2012

(65) Prior Publication Data
US 2013/0185644 A1 Jul. 18, 2013

(30) Foreign Application Priority Data
Oct. 1, 2010 (JP) .................. 2010-224308

(51) Int. Cl.
*H04L 12/24* (2006.01)
*G06F 17/30* (2006.01)
*G06F 19/12* (2011.01)
(Continued)

(52) U.S. Cl.
CPC .......... *H04L 41/22* (2013.01); *G06F 17/30958* (2013.01); *G06F 19/12* (2013.01); *G06F 19/26* (2013.01); *G06F 19/28* (2013.01)

(58) Field of Classification Search
None
See application file for complete search history.

(56) References Cited

U.S. PATENT DOCUMENTS

| 2005/0154535 A1* | 7/2005 | Sun et al. ................. 702/19 |
| 2005/0188294 A1* | 8/2005 | Kuchinsky et al. ........ 715/500 |
| 2009/0138251 A1* | 5/2009 | Bugrim et al. ............. 703/11 |

FOREIGN PATENT DOCUMENTS

| JP | 2003-186894 A | 7/2003 |
| WO | WO 2005/096207 A1 | 10/2005 |

OTHER PUBLICATIONS

Japanese Office Action issued Jul. 8, 2014, in Japanese Patent Application No. 2013-159876.

(Continued)

*Primary Examiner* — Phenuel Salomon
*Assistant Examiner* — Tuan S Nguyen
(74) *Attorney, Agent, or Firm* — Oblon, McClelland, Maier & Neustadt, L.L.P.

(57) ABSTRACT

The present invention involves retrieving edges that do not constitute a designated network model which is a network model designated by a user and are linked to nodes that constitute the designated network model, displaying retrieval results that include the retrieved edges and network model IDs corresponding to the edges in a selectable manner, and generating an integrated network model in which, when the retrieval results are selected by the user, the edges that are included in the selected retrieval results and the nodes that do not constitute the designated network model and are linked to the edges, are integrated into the designated network model.

27 Claims, 13 Drawing Sheets

(51) Int. Cl.
   G06F 19/26  (2011.01)
   G06F 19/28  (2011.01)

(56) References Cited

OTHER PUBLICATIONS

Decision of a Patent Grant issued Oct. 7, 2014, in Japanese Patent Application No. 2013-159876 with English translation.
Extended Search Report issued Mar. 17, 2014 in European Patent Application No. 11828514.7.
Zhenjun Hu, et al., "VisANT: data-integrating visual framework for biological networks and modules", Nucleic Acids Research, vol. 33, Web Server issue, Jul. 1, 2005, XP055106006, pp. W352-W357.
Paul Shannon, et al., "Cytoscape: A Software Environment for Integrated Models of Biomolecular Interaction Networks", Genome Research, vol. 13, No. 11, Nov. 1, 2003, XP055105995, pp. 2498-2504.
Lars Juhl Jensen, et al., "Literature mining for the biologist: from information retrieval to biological discovery", Nature Reviews Genetics, vol. 7, Feb. 1, 2006, XP007902199, pp. 119-129.
Funahashi, A., et al., "CellDesigner: a process diagram editor for gene-regulatory and biochemical networks," BIOSILICO, vol. 1, No. 5, pp. 159-162, (Nov. 2003).
Funahashi, A., et al., "CellDesigner 3.5: A Versatile Modeling Tool for Biochemical Networks," Proceedings of the IEEE, vol. 96, No. 8, pp. 1254-1265, (Aug. 2008).
Matsuoka, Y., et al., "Payao: A Community Platform for SBML Pathway Model Curation," Bioinformatics Advance Access, vol. 26, No. 10, pp. 1-3, (Apr. 5, 2010).
Oda, K., et al., "A comprehensive pathway map of epidermal growth factor receptor signaling," Molecular Systems Biology, No. 2005.0010, pp. 1-17, (2005).
Oda, K., et al., "A comprehensive map of the toll-like receptor signaling network," Molecular Systems Biology, No. 2006.0015, pp. 1-20, (2006).
Bauer-Mehren, A., et al., "Pathway databases and tools for their exploitation: benefits, current limitations and challenges," Molecular Systems Biology, vol. 5, No. 290, pp. 1-13, (2009).
"Ingenuity IPA Software-Microarray Analysis, Pathway Analysis, Biomarkers," http://www.ingenuity.com/products/pathways_analysis.html, pp. 1-10, (Sep. 4, 2010).
"MetaCore," http://www.genego.com/metacore.php, Total 7 Pages, (Sep. 5, 2010).
"NextBio," http://www.nextbio.com/b/nextbio.nb, Total 2 Pages, (Sep. 4, 2010).
International Search Report Issued May 24, 2011 in PCT/JP2011/058323.
Nicolas Le Novére et al., "The Systems Biology Graphical Notation", Nature Biotechnology, vol. 27, No. 8, Aug. 2009, pp. 735-741.
Hiroaki Kitano et al., "Computational Infrastructure for Systems Biology", Journal of the Society of Instrument and Control Engineers, vol. 49, No. 8, Aug. 10, 2010, pp. 507-512 with cover pages.

* cited by examiner

NETWORK MODEL INTEGRATION DEVICE, NETWORK MODEL INTEGRATION SYSTEM, NETWORK MODEL INTEGRATION METHOD, AND COMPUTER PROGRAM PRODUCT

TECHNICAL FIELD

The present invention relates to a network model integration device, a network model integration system, a network model integration method, and a computer program product.

BACKGROUND ART

Conventionally, a technique of providing a network that includes information related to biology has been known.

The intermolecular network model creation and editing software described in Non Patent Literatures 1 and 2 disclose a technique of acquiring information by connecting to an external literature database, a pathway database, a text mining device, and the like during editing of pathways in an intermolecular network.

The online system described in Non Patent Literature 3 discloses a technique of generating databases of a network model created by the CellDesigner which is a network modeling tool and displaying the network model on the Internet. The online system further discloses a technique of allowing user to add information such as adding of interfaces such as tags and comments on a pathway model.

The pathway map display systems described in Non Patent Literatures 4 to 6 disclose a technique of generating a pathway map that is more accurate than the conventional network modeling tool using the CellDesigner.

The ingenuity pathway analysis (IPA) software described in Non Patent Literature 7 discloses a technique of storing unique literature databases and network model databases to allow users to perform modeling, analysis, displaying, retrieval, and the like of complex biological and chemical systems.

The pathway analysis system described in Non Patent Literature 8 discloses a technique of allowing users to upload interaction data and map pathway-related experimental data, provide databases of interaction data, evaluate biological influence of low-molecular compounds including pathway analysis, edit pathways, and retrieve compound data.

The web application described in Non Patent Literature 9 discloses a technique of providing and sharing data by connecting to relevant databases that store public data, papers, clinical trials, and science news related to biology.

CITATION LIST

Non Patent Literature

Non Patent Literature 1: Funahashi, A., Tanimura, N., Morohashi, M., and Kitano, H., CellDesigner: a process diagram editor for gene-regulatory and biochemical networks, BIOSILICO, Volume 1, Issue 5, 5 Nov. 2003, Pages 159-162

Non Patent Literature 2: Funahashi, A.; Matsuoka, Y.; Jouraku, A.; Morohashi, M.; Kikuchi, N.; Kitano, H. "Cell-Designer 3.5: A Versatile Modeling Tool for Biochemical Networks" Proceedings of the IEEE Volume 96, Issue 8, August 2008: 1254-1265

Non Patent Literature 3: Matsuoka Y, Ghosh S, Kikuchi N, Kitano H., Payao: a community platform for SBML pathway model curation., Bioinformatics. 2010 May 15; 26(10):1381-3. Epub 2010 Apr. 5.

Non Patent Literature 4: Oda K, Matsuoka Y, Funahashi A, Kitano H., A comprehensive pathway map of epidermal growth factor receptor signaling., Mol Syst Biol. 2005; 1:2005.0010. Epub 2005 May 25.

Non Patent Literature 5: Oda K, Kitano H., A comprehensive map of the toll-like receptor signaling network., Mol Syst Biol. 2006; 2:2006.0015. Epub 2006 Apr. 18.

Non Patent Literature 6: Bauer-Mehren A, Furlong L I, Sanz F., Pathway databases and tools for their exploitation: benefits, current limitations and challenges., Mol Syst Biol. 2009; 5:290. Epub 2009 Jul. 28.

Non Patent Literature 7: Ingenuity Systems Inc. (http://www.ingenuity.com)

Non Patent Literature 8: GeneGo Inc. (http://www.genego.com/)

Non Patent Literature 9: NextBio (http://www.nextbio.com/b/nextbio.nb)

SUMMARY OF INVENTION

Problem to be Solved by the Invention

However, the conventional pathway analysis systems disclosed in Non Patent Literatures 1 to 9 have a problem in that, when the pathway model data uploaded by the user is expanded, it is not possible to present candidates for interactions or the like retrieved from various information sources to the user and to integrate candidates selected by the user. Moreover, the conventional pathway analysis systems have another problem in that the information sources or the like of the retrieval results that serve as the basis for presenting the candidates that are to be newly integrated are not displayed so as to be identified by the user.

The present invention has been made in view of the above problems, and an object of the present invention is to provide a network model integration device, a network model integration system, a network model integration method, and a computer program product capable of displaying a network model of information related to biology such as an intermolecular interaction network, a transcription control network, an intercellular communication, or an inter-organ interaction and expanding the network model based on a user's selection.

Means for Solving Problem

In order to attain this object, a network model integration device according to one aspect of the present invention is a network model integration device comprising an input unit, a display unit, a storage unit, and a control unit, wherein the storage unit includes a network model storage unit that stores a network model that includes nodes that represent constituent elements of a biological object and edges that represent interactions between the constituent elements and a network model ID that identifies the network model in association, and the control unit includes a retrieving unit that, when the network model is designated by a user via the input unit, retrieves the edges that are stored in the network model storage unit, do not constitute a designated network model which is the network model, and are linked to the nodes that constitute the designated network model, and a retrieval result displaying unit that displays retrieval results including the edges retrieved by the retrieving unit and the network model ID that identifies the network model including the edges stored in the network model storage unit on the display unit in a selectable manner, an integrating unit that, when the retrieval results displayed on the display unit by the retrieval result displaying unit are selected by the user via the input unit, generates an integrated network model which is the network model in which the edges included in the selected retrieval results and the nodes that do not constitute the designated network model and are linked to the edges are integrated into the designated network model, and a network model storing unit that acquires the network model ID that identifies the integrated network model generated by the integrating unit and stores the integrated network model and the network model ID in the network model storage unit in association.

The network model integration device according to another aspect of the present invention is the network model integration device, wherein the designated network model is the network model stored in the network model storage unit, an existing network model that is not stored in the network model storage unit, or a new network model.

The network model integration device according to still another aspect of the present invention is the network model integration device, wherein when the existing network model or the new network model is input by the user via the input unit, the network model storing unit further acquires the network model ID that identifies the designated network model and stores the designated network model and the network model ID in the network model storage unit in association.

The network model integration device according to still another aspect of the present invention is the network model integration device, wherein when an ID selection instruction is input by the user via the input unit, the network model storing unit acquires the network model ID that identifies the designated network model, included in the integrated network model or a new network model ID as a network model ID that identifies the integrated network model based on the ID selection instruction and stores the integrated network model and the network model ID in the network model storage unit in association.

The network model integration device according to still another aspect of the present invention is the network model integration device, wherein the storage unit further includes a pathway storage unit that stores pathways of the constituent elements, a literature information storage unit that stores literature information on literatures related to the constituent elements and the interactions, a news storage unit that stores news provided by a news delivery service, and a text mining storage unit that stores text information on the constituent elements and the interactions that are extracted from the literature information using text mining, the retrieving unit further retrieves the edges that do not constitute the designated network model and are linked to the nodes that constitute the designated network model from any one or all of the pathways stored in the pathway storage unit, the literature information stored in the literature information storage unit, the news stored in the news storage unit, and the text information stored in the text mining storage unit and acquires the network model ID that identifies the network model that includes the edges.

The network model integration device according to still another aspect of the present invention is the network model integration device, wherein the retrieving unit retrieves the edges that are designated in advance by the user via the input unit.

The network model integration device according to still another aspect of the present invention is the network model integration device, wherein the retrieval result displaying unit further displays the retrieval results including the nodes that do not constitute the designated network model and are linked to the edges retrieved by the retrieving unit and the network model ID that identifies the network model that includes the nodes stored in the network model storage unit on the display unit in a selectable manner.

The network model integration device according to still another aspect of the present invention is the network model integration device, wherein the retrieval result displaying unit performs any one or both of a process of displaying the retrieval results on the display unit in a selectable manner in a list form and a process of displaying the retrieval results on the display unit so as to be superimposed on the network model.

The network model integration device according to still another aspect of the present invention is the network model integration device, wherein the control unit further includes a configuration notifying unit that, when the edges stored in the network model storage unit are retrieved by the retrieving unit, notifies the user, who has provided the network model, of any one or both of the nodes and edges that are included in the designated network model and are not included in the network model stored in the network model storage unit, identified by the network model ID corresponding to the edges.

The network model integration device according to still another aspect of the present invention is the network model integration device, wherein the control unit further includes a configuration notifying unit that, when the integrated network model is generated by the integrating unit, notifies the user, who has provided the network model, of any one or both of the nodes and edges that are included in the integrated network model and are not included in the network model stored in the network model storage unit, identified by the network model ID corresponding to the edges that are included in the retrieval results that are selected by the user via the input unit.

The network model integration device according to still another aspect of the present invention is the network model integration device, wherein the network model storage unit further stores notes for a portion or all of the network models, the nodes, or the edges in association with the portion or all of the network models, the nodes, or the edges, and the control unit further includes a note storing unit that, when the notes are input by the user via the input unit with respect to the portion or all of the network models, the nodes included in the network model, or the edges included in the network model, stored in the network model storage unit, stores the notes in the network model storage unit in association with the portion or all of the network models, the nodes, or the edges, and a note notifying unit that notifies the user, who has provided the network model corresponding to the notes, the network model that includes the nodes corresponding to the notes, or the network model that includes the edges corresponding to the notes, stored in the network model storage unit, of the notes stored in the network model storage unit.

The network model integration device according to still another aspect of the present invention is the network model integration device, wherein the network model storage unit further stores evaluation values on the retrieval results in association with the edges included in the retrieval results, and the control unit further includes an evaluation value storing unit that, when evaluation values on the retrieval results are input by the user via the input unit, stores the evaluation values in the network model storage unit in association with the edges included in the retrieval results.

The network model integration device according to still another aspect of the present invention is the network model integration device, wherein the evaluation values are input when the retrieval results displayed on the display unit by the retrieval result displaying unit are selected.

The network model integration device according to still another aspect of the present invention is the network model integration device, wherein the retrieval result displaying unit further displays the evaluation values that are stored in the network model storage unit and correspond to the edges retrieved by the retrieving unit on the display unit.

The network model integration device according to still another aspect of the present invention is the network model integration device, wherein the control unit further includes a keyword acquiring unit that, when a portion or all of the network models, the nodes, or the edges are selected by the user via the input unit, acquires keywords related to the portion or all of the network models, the nodes, or the edges, a literature information retrieving unit that retrieves the literature information on the literatures that are issued within a predetermined period and are stored in the literature information storage unit using the keywords acquired by the keyword acquiring unit at intervals that are set by the user via the input unit, and a literature information displaying unit that performs any one or both of a process of displaying the literature information retrieved by the literature information retrieving unit on the display unit in a list form and a process of displaying the literature information on the display unit so as to be superimposed on the network model stored in the network model storage unit.

The network model integration device according to still another aspect of the present invention is the network model integration device, wherein the control unit further includes a literature information notifying unit that notifies the user of the literature information retrieved by the literature information retrieving unit.

The network model integration device according to still another aspect of the present invention is the network model integration device, wherein the literature information displaying unit performs any one or both of the process of displaying the literature information on the display unit in the list form and the process of displaying the literature information on the display unit so as to be superimposed on the network model based on display preference conditions that are set by the user via the input unit.

The network model integration device according to still another aspect of the present invention is the network model integration device, wherein the display preference conditions are literature names, literature issuing organization names, or book titles.

The network model integration device according to still another aspect of the present invention is the network model integration device, wherein the storage unit further includes an advertisement information storage unit that stores advertisement information on the constituent elements or the interactions, and the control unit further includes an advertisement information acquiring unit that, when a portion or all of the network models, the nodes, or the edges are selected by the user via the input unit, acquires the advertisement information that is stored in the advertisement information storage unit and is related to the constituent elements or the interactions that are based on the portion or all of the network models, the nodes, or the edges, and an advertisement information displaying unit that displays the advertisement information acquired by the advertisement information acquiring unit on the display unit.

The network model integration device according to still another aspect of the present invention is the network model integration device, wherein the advertisement information acquiring unit further acquires the advertisement information that is stored in the advertisement information storage unit and is related to neighboring constituent elements that interact with the constituent elements that are based on the portion or all of the network models, the nodes, or the edges.

The network model integration device according to still another aspect of the present invention is the network model integration device, wherein the storage unit further includes an advertisement information storage unit that stores advertisement information related to the constituent elements or the interactions, and the control unit further includes a network model displaying unit that displays the network model on the display unit, an advertisement information acquiring unit that recognizes a portion of the network model that is displayed at a center of a screen for the longest period within a predetermined period by the network model displaying unit and acquires the advertisement information that is stored in the advertisement information storage unit and is related to any one or both of the constituent elements based on the nodes and the interactions based on the edges, included in the portion of the network model, and an advertisement information displaying unit that displays the advertisement information acquired by the advertisement information acquiring unit on the display unit.

The network model integration device according to still another aspect of the present invention is the network model integration device, wherein the control unit further includes a literature model acquiring unit that acquires the network model from the literature information in which the edges are retrieved by the retrieving unit using natural language analysis and acquires a network model ID that identifies the network model, and the network model storing unit further stores the network model acquired by the literature model acquiring unit and the network model ID in the network model storage unit in association.

A network model integration system according to still another aspect of the present invention is a network model integration system comprising a network model integration device including a control unit and a storage unit and a terminal device including an input unit, a display unit, and a control unit that are connected to each other in a communicable manner, wherein the storage unit of the network model integration device includes a network model storage unit that stores a network model that includes nodes that represent constituent elements of a biological object and edges that represent interactions between the constituent elements and a network model ID that identifies the network model in association, the control unit of the network model integration device includes a retrieving unit that retrieves the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device, an integrating unit that generates an integrated network model which is the network model in which the edges included in the retrieval results that are transmitted from the terminal device and are selected by the user via the input unit and the nodes that do not constitute the designated network model and are linked to the edges are integrated into the designated network model, and a network model storing unit that acquires the network model ID that identifies the integrated network model generated by the integrating unit and stores the integrated network model and the network model ID in the network model storage unit in association, and the control unit of the terminal device includes a retrieval result displaying unit that displays the retrieval results transmitted from the network model integration device on the display unit in a selectable manner and transmits the retrieval results selected by the user via the input unit to the terminal device.

A network model integration method according to still another aspect of the present invention is a network model integration method executed by a network model integration device including an input unit, a display unit, a storage unit, and a control unit, wherein the storage unit includes a network model storage unit that stores a network model that includes nodes that represent constituent elements of a biological object and edges that represent interactions between the constituent elements and a network model ID that identifies the network model in association, the method executed by the control unit comprising a retrieving step of retrieving the edges that are stored in the network model storage unit, do not constitute a designated network model which is the network model, and are linked to the nodes that constitute the designated network model, when the network model is designated by a user via the input unit, and a retrieval result displaying step of displaying retrieval results including the edges retrieved at the retrieving step and the network model ID that identifies the network model including the edges stored in the network model storage unit on the display unit in a selectable manner, an integrating step of generating an integrated network model which is the network model in which the edges included in the selected retrieval results and the nodes that do not constitute the designated network model and are linked to the edges are integrated into the designated network model, when the retrieval results displayed on the display unit at the retrieval result displaying step are selected by the user via the input unit, and a network model storing step of acquiring the network model ID that identifies the integrated network model generated at the integrating step and storing the integrated network model and the network model ID in the network model storage unit in association.

A network model integration method according to still another aspect of the present invention is a network model integration method that is performed in a network model integration system including a network model integration device including a control unit and a storage unit and a terminal device including an input unit, a display unit, and a control unit that are connected to each other in a communicable manner, wherein the storage unit of the network model integration device includes a network model storage unit that stores a network model that includes nodes that represent constituent elements of a biological object and edges that represent interactions between the constituent elements and a network model ID that identifies the network model in association, the method comprising a retrieving step of retrieving the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device that is performed by the control unit of the network model integration device, a retrieval result displaying step of displaying the retrieval results transmitted from the network model integration device on the display unit in a selectable manner and transmits the retrieval results selected by the user via the input unit to the terminal device that is performed by the control unit of the terminal apparatus, an integrating step of generates an integrated network model which is the network model in which the edges included in the retrieval results that are transmitted from the terminal device and are selected by the user via the input unit and the nodes that do not constitute the designated network model and are linked to the edges are integrated into the designated network model that is performed by the control unit of the network model integration device, and a network model storing step of acquires the network model ID that identifies the integrated network model generated at the integrating step and storing the integrated network model and the network model ID in the network model storage unit in association that is performed by the control unit of the network model integration device.

A computer program product according to still another aspect of the present invention is a computer program product having a non-transitory computer readable mediums including programmed instructions for a network model integration method executed by a network model integration device including an input unit, a display unit, a storage unit, and a control unit, wherein the storage unit includes a network model storage unit that stores a network model that includes nodes that represent constituent elements of a biological object and edges that represent interactions between the constituent elements and a network model ID that identifies the network model in association, wherein the instructions, when executed by the control unit, cause the control unit to execute a retrieving step of retrieving the edges that are stored in the network model storage unit, do not constitute a designated network model which is the network model, and are linked to the nodes that constitute the designated network model, when the network model is designated by a user via the input unit, and a retrieval result displaying step of displaying retrieval results including the edges retrieved at the retrieving step and the network model ID that identifies the network model including the edges stored in the network model storage unit on the display unit in a selectable manner, an integrating step of generating an integrated network model which is the network model in which the edges included in the selected retrieval results and the nodes that do not constitute the designated network model and are linked to the edges are integrated into the designated network model, when the retrieval results displayed on the display unit at the retrieval result displaying step are selected by the user via the input unit, and a network model storing step of acquiring the network model ID that identifies the integrated network model generated at the integrating step and stores the integrated network model and the network model ID in the network model storage unit in association.

A computer program product according to still another aspect of the present invention is a computer program product having a non-transitory computer readable mediums including programmed instructions for a network model integration method executed by a network model integration device including a control unit and a storage unit that is connected to a terminal device including an input unit in a communicable manner, wherein the storage unit includes a network model storage unit that stores a network model that includes nodes that represent constituent elements of a biological object and edges that represent interactions between the constituent elements and a network model ID that identifies the network model in association, wherein the instructions, when executed by the control unit, cause the control unit to execute a retrieving step of retrieving the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device, an integrating step of generates an integrated network model which is the network model in which the edges included in the retrieval results that are transmitted from the terminal device and are selected by the user via the input unit and the nodes that do not constitute the designated network model and are linked to the edges are integrated into the designated network model, and a network model storing step of acquires the network model ID that identifies the integrated network model generated at the integrating step and stores the integrated network model and the network model ID in the network model storage unit in association.

Effect of the Invention

The present invention, when the network model is designated by a user via the input unit, retrieves the edges, do not constitute a designated network model which is the network model, and are linked to the nodes that constitute the designated network model, and displays retrieval results including the edges retrieved and the network model ID that identifies the network model including the edges on the display unit in a selectable manner, when the retrieval results displayed on the display unit are selected by the user via the input unit, generates an integrated network model which is the network model in which the edges included in the selected retrieval results and the nodes that do not constitute the designated network model and are linked to the edges are integrated into the designated network model, and acquires the network model ID that identifies the integrated network model generated and stores the integrated network model and the network model ID in association. Thus, an effect is realized that the user can determine the reliability or the like of the information sources that serve as the basis for presenting the edges, and the network model can be expanded to a highly reliable network model by integrating the edges selected by the user based on the information sources into the network model.

According to the present invention, the designated network model is the network model stored in the storage unit, an existing network model that is not stored in the storage unit, or a new network model. Thus, an effect is realized that the newly identified network models can be expanded and various existing network models can be expanded.

The present invention, when the existing network model or the new network model is input by the user via the input unit, further acquires the network model ID that identifies the designated network model and stores the designated network model and the network model ID in the storage unit in association. Thus, an effect is realized that the user can search the information sources or the like that serve as the basis for presenting the network models that are newly registered in this system.

The present invention, when an ID selection instruction is input by the user via the input unit, acquires the network model ID that identifies the designated network model, included in the integrated network model or a new network model ID as a network model ID that identifies the integrated network model based on the ID selection instruction and stores the integrated network model and the network model ID in the storage unit in association. Thus, an effect is realized that the user can select whether a new network model ID will be assigned to the integrated network model in which the edges selected by the user are integrated or the network model ID of the designated network model will be used according to the user's convenience.

The present invention further retrieves the edges that do not constitute the designated network model and are linked to the nodes that constitute the designated network model from any one or all of the pathways stored in the storage unit, the literature information stored in the storage unit, the news stored in the storage unit, and the text information stored in the storage unit and acquires the network model ID that identifies the network model that includes the edges. Thus, an effect is realized that edge retrieval targets can be expanded to various information sources.

The present invention retrieves the edges that are designated in advance by the user via the input unit. Thus, an effect is realized that the user can filter the retrieval targets of the system.

The present invention further displays the retrieval results including the nodes that do not constitute the designated network model and are linked to the edges retrieved and the network model ID that identifies the network model that includes the nodes stored in the storage unit on the display unit in a selectable manner. Since the retrieval results include both edges and nodes, an effect is realized that the user can determine the reliability or the like of the information sources that serve as the basis for presenting the nodes.

The present invention performs any one or both of a process of displaying the retrieval results on the display unit in a selectable manner in a list form and a process of displaying the retrieval results on the display unit so as to be superimposed on the network model. Thus, an effect is realized that the retrieval results can be selectively displayed in such a form that information is easily organized and in such a form that information is easily visible.

The present invention, when the edges stored in the storage unit are retrieved, notifies the user, who has provided the network model, of any one or both of the nodes and edges that are included in the designated network model and are not included in the network model stored in the storage unit, identified by the network model ID corresponding to the edges. Thus, an effect is realized that the user can understand in real time the possibility of progress in researches on the network model provided by the user and the neighboring researches.

The present invention, when the integrated network model is generated, notifies the user, who has provided the network model, of any one or both of the nodes and edges that are included in the integrated network model and are not included in the network model stored in the storage unit, identified by the network model ID corresponding to the edges that are included in the retrieval results that are selected by the user via the input unit. Thus, when the network model is expanded, an effect is realized that a person who has provided a network model including the edges that are integrated into the expanded integrated network model to this system can be informed of the expansion.

The present invention, when the notes are input by the user via the input unit with respect to the portion or all of the network models, the nodes included in the network model, or the edges included in the network model, stored in the storage unit, stores the notes in the storage unit in association with the portion or all of the network models, the nodes, or the edges, and notifies the user, who has provided the network model corresponding to the notes, the network model that includes the nodes corresponding to the notes, or the network model that includes the edges corresponding to the notes, stored in the storage unit, of the notes stored in the storage unit. Thus, when the user evaluates the network model, an effect is realized that the user can obtain information for making a decision other than information sources.

The present invention, when evaluation values on the retrieval results are input by the user via the input unit, stores the evaluation values in the storage unit in association with the edges included in the retrieval results. Thus, an effect is realized that the user can objectively understand the reliability on the edges stored in the system.

According to the present invention, the evaluation values are input when the retrieval results displayed on the display unit are selected. Thus, an effect is realized that a process of adding evaluations on the edges can be automatically performed simultaneously with the process of the user integrating edges into the network model.

The present invention further displays the evaluation values that are stored in the storage unit and correspond to the edges retrieved on the display unit. Thus, an effect is realized that the user can visually understand evaluations that another user has added to the edges that constitute the network model.

The present invention, when a portion or all of the network models, the nodes, or the edges are selected by the user via the input unit, acquires keywords related to the portion or all of the network models, the nodes, or the edges, retrieves the literature information on the literatures that are issued within a predetermined period and are stored in the storage unit using the keywords acquired at intervals that are set by the user via the input unit, and performs any one or both of a process of displaying the literature information retrieved on the display unit in a list form and a process of displaying the literature information on the display unit so as to be superimposed on the network model stored in the storage unit. Thus, an effect is realized that the user can find latest papers on the network model that the user is interested in without performing a complicated literature retrieving process using a method of setting literature information retrieval and a push-type information transfer function.

The present invention notifies the user of the literature information retrieved. Thus, an effect is realized that the latest papers on the interested network model can be received via an email or the like without performing a complicated literature retrieving process.

The present invention performs any one or both of the process of displaying the literature information on the display unit in the list form and the process of displaying the literature information on the display unit so as to be superimposed on the network model based on display preference conditions that are set by the user via the input unit. Thus, an effect is realized that papers that are actually displayed can be selected from the retrieved papers based on a filter that is set in advance.

According to the present invention, the display preference conditions are literature names, literature issuing organization names, or book titles. Thus, an effect is realized that papers that are posted on publications that are believed by researchers to be highly reliable and papers issued by highly reliable researchers only can be displayed.

The present invention, when a portion or all of the network models, the nodes, or the edges are selected by the user via the input unit, acquires the advertisement information that is stored in the storage unit and is related to the constituent elements or the interactions that are based on the portion or all of the network models, the nodes, or the edges, and displays the advertisement information acquired on the display unit. Thus, an effect is realized that announcements of appropriate advertisements that the user is interested in can be displayed using a plurality of items of information or information on singular or plural elements selected by the user, displayed on the screen.

The present invention further acquires the advertisement information that is stored in the storage unit and is related to neighboring constituent elements that interact with the constituent elements that are based on the portion or all of the network models, the nodes, or the edges. Thus, an effect is realized that advertisements appropriate for elements that the user is interested in can be also displayed.

The present invention displays the network model on the display unit, recognizes a portion of the network model that is displayed at a center of a screen for the longest period within a predetermined period and acquires the advertisement information that is stored in the storage unit and is related to any one or both of the constituent elements based on the nodes and the interactions based on the edges, included in the portion of the network model, and displays the advertisement information acquired on the display unit. Thus, an effect is realized that advertisements appropriate for an object of interest which is often displayed near the center of the screen for a long period can be displayed.

The present invention acquires the network model from the literature information in which the edges are retrieved using natural language analysis and acquires a network model ID that identifies the network model, and further stores the network model acquired and the network model ID in the storage unit in association. Thus, an effect is realized that the network model can be automatically generated from the literature information of papers or the like and presented to the user.

MODE(S) FOR CARRYING OUT THE INVENTION

The following describes an embodiment of a network model integration device, a network model integration system, a network model integration method, and a program according to the present invention in detail with reference to the drawings below. The present invention is not limited to the embodiments.

In the following embodiment, in particular, although an example in which the present invention is applied to an inter-molecular interaction network within a biological object is explained, the present invention is not limited to this case, but can be equally applied to all technical fields in which information related to biology such as a transcription control network, an intercellular communication, and an inter-organ interaction is provided in the form of a network using a program or a web application.

Overview of Embodiment of Present Invention

Figure 1:
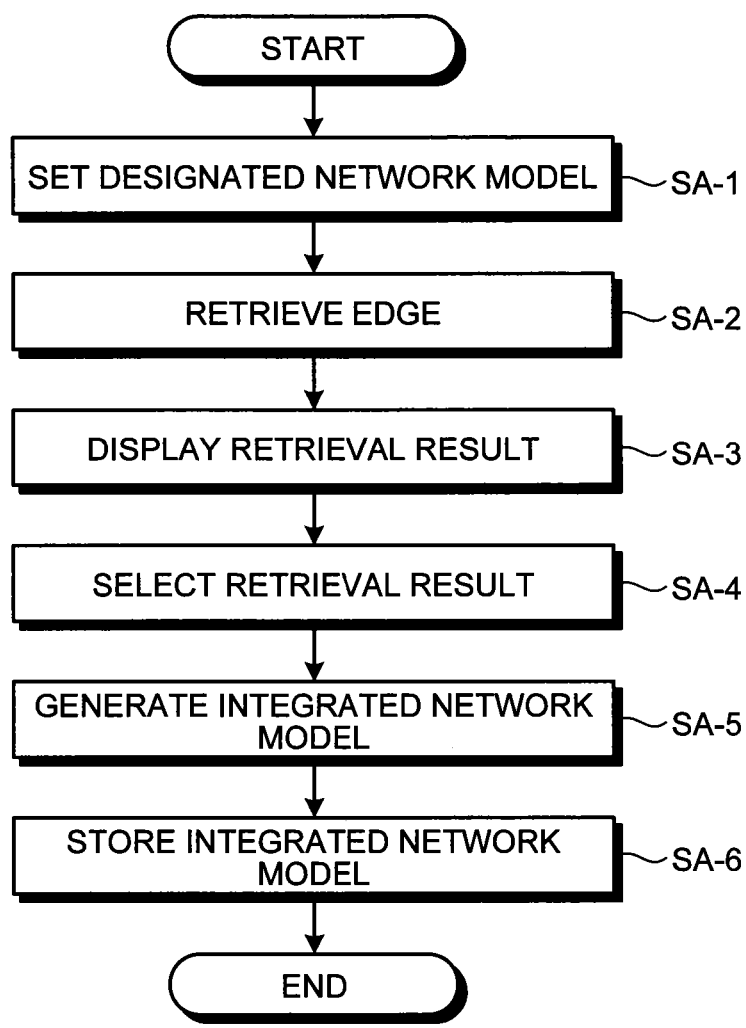
FIG. 1 is a flowchart illustrating a basic principle of the present embodiment.

Hereinafter, an overview of an embodiment of the present invention will be explained with reference to FIG. 1. After that, the configuration, the process, and the like of the present embodiment will be explained in detail. FIG. 1 is a flowchart illustrating a basic principle of the present embodiment.

The present embodiment schematically has the following basic features. In other words, when a network model that includes nodes that represent constituent elements of a biological object and edges that represent interactions between the constituent elements is designated by a user, as shown in FIG. 1, a control unit of a network model integration device according to the present embodiment sets the network model as a designated network model (step SA-1). Here, the designated network model may be a network model stored in a storage unit, an existing network model that is not stored in the storage unit, or a new network model. The existing network model may be information that can be acquired from an external database or the like via the Internet. When an existing network model or a new network model is input by the user, the control unit may acquire a network model ID that identifies the designated network model and associate the designated network model and the network model ID to store in the storage unit.

The control unit of the network model integration device retrieves edges that do not constitute the designated network model and are stored in the storage unit and are linked to the nodes that constitute the designated network model set in step SA-1 (step SA-2). Here, the control unit may further retrieve the edges that do not constitute the designated network model and are linked to the nodes that constitute the designated network model from any one or all of a pathway of the constituent elements stored in the storage unit, literature information of literatures related to the constituent elements and interactions stored in the storage unit, the news provided by a news delivery service stored in the storage unit, and text information related to the constituent elements and interactions that are extracted from the literature information stored in the storage unit using natural language analysis and acquire network model IDs that identify network models including the edges. Further, the control unit may retrieve edges stored in the storage unit, designated in advance by the user.

The control unit of the network model integration device displays retrieval results that include the retrieved edges and network model IDs that identify the network models including the edges stored in the storage unit on a display unit in a selectable manner (step SA-3). Here, the control unit may further display retrieval results that include the nodes that do not constitute the designated network model and are linked to the retrieved edges and network model IDs that identify the network models including the nodes stored in the storage unit. Further, the control unit may perform any one or both of a process of displaying the retrieval results on the display unit in a list form in a selectable manner and a process of displaying the retrieval results on the display unit so as to be superimposed on the network model. Furthermore, the control unit may further display evaluation values on the retrieval results stored in the storage unit, corresponding to the retrieved edges on the display unit.

When the retrieval results displayed on the display unit are selected by the user, the control unit of the network model integration device detects the selection (step SA-4).

The control unit of the network model integration device generates an integrated network model which is a network model in which the edges included in the retrieval results selected by the user and the nodes that do not constitute the designated network model and are linked to the edges are integrated into the designated network model (step SA-5).

The control unit of the network model integration device acquires a network model ID that identifies the generated integrated network model and associates the integrated network model and the network model ID to store in the storage unit (step SA-6). In this way, the process ends. When an ID selection instruction is input by the user, the control unit may acquire the network model ID that identifies the designated network model, included in the integrated network model or a new network model ID as a network model ID that identifies the integrated network model based on the ID selection instruction and associate the integrated network model and the network model ID to store in the storage unit.

Hereinabove, an overview of the present embodiment has been explained.

Embodiment of Network Model Integration System

Next, an embodiment of a network model integration system will be explained with reference to FIGS. 2 to 10. An embodiment of a standalone-type network model integration system explained below is used for illustrating a network model integration system that embodies the technical idea of the present invention but is not intended to limit the present invention to the network model integration system and can be equally applied to network model integration systems of the other embodiments included in the claims.

Configuration of Network Model Integration System 10

Figure 2:
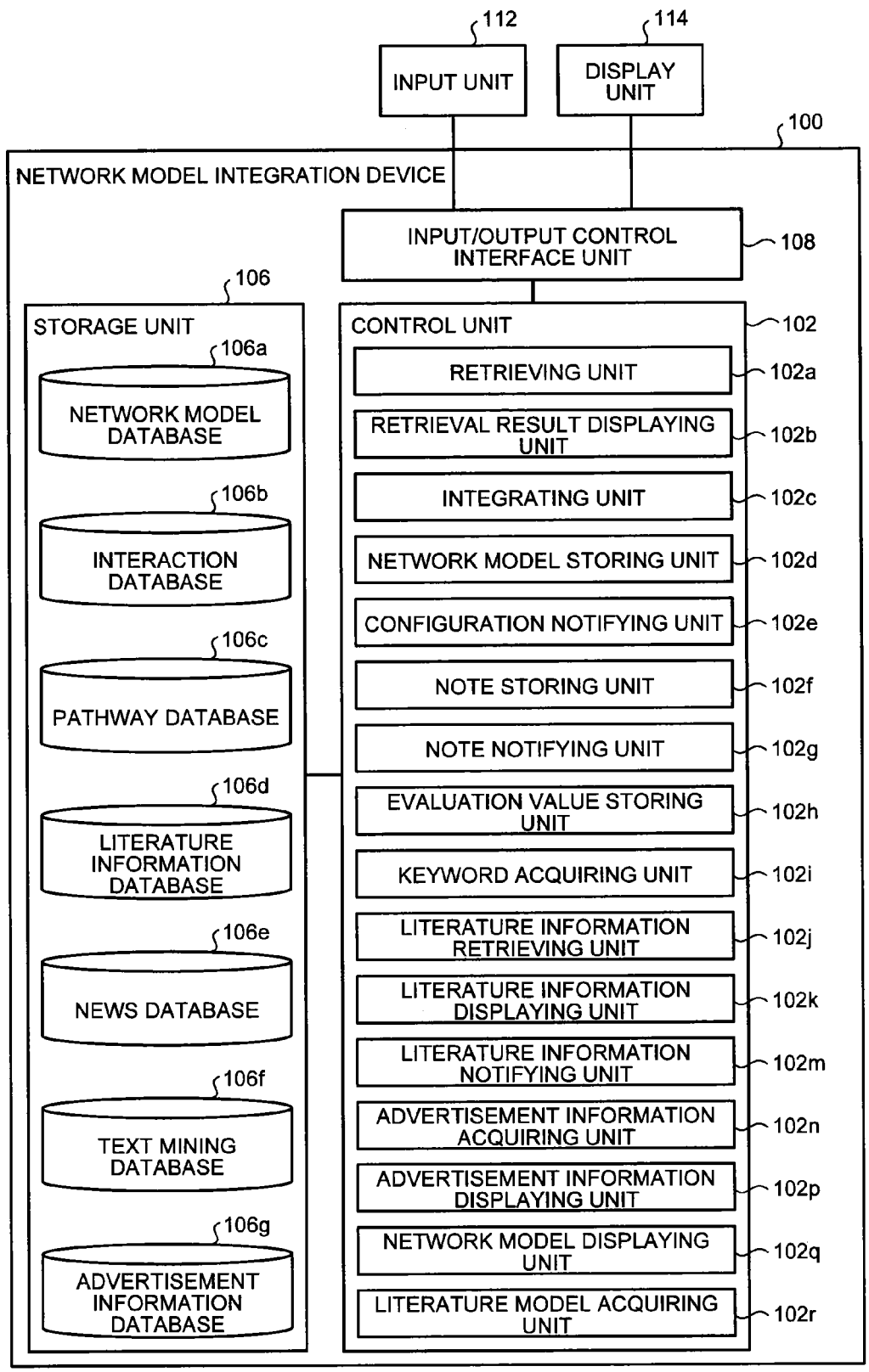
FIG. 2 is a block diagram illustrating an example of the configuration of a network model integration system 10 to which the present embodiment is applied.
Figure 3:
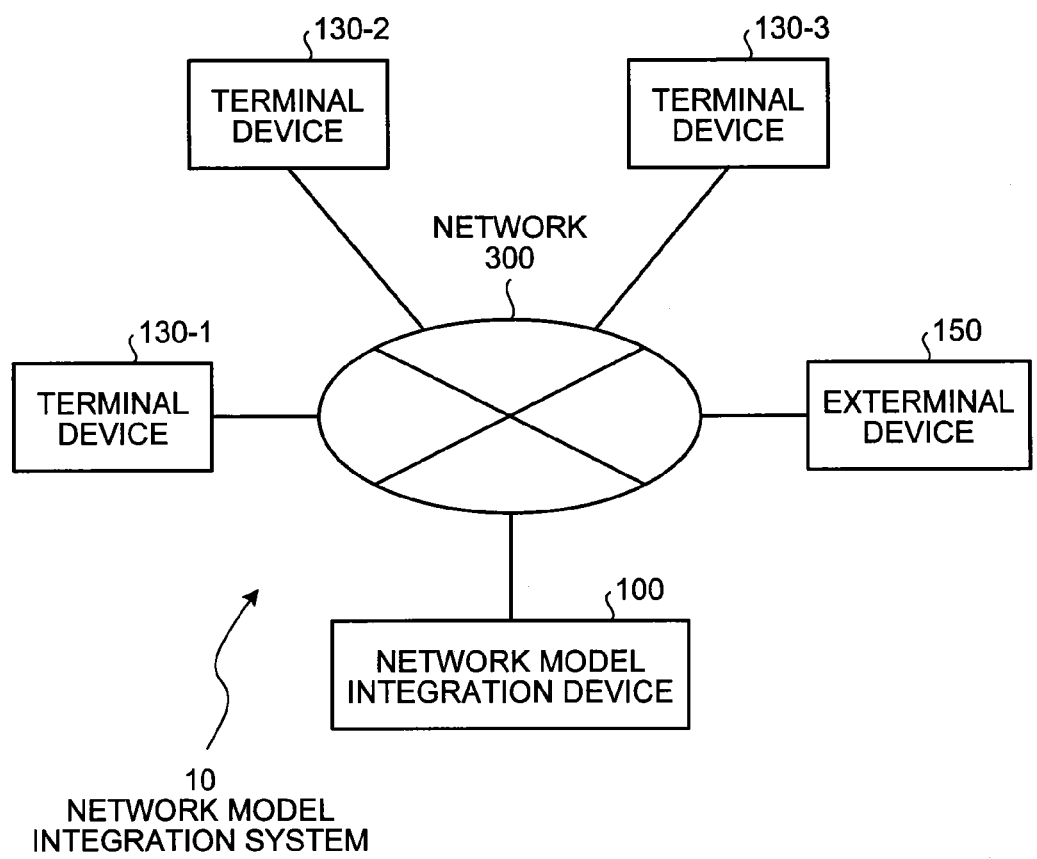
FIG. 3 is a conceptual diagram illustrating an example of an overall configuration of the network model integration system 10 according to the present embodiment.

First, the configuration of a network model integration system 10 will be explained with reference to FIG. 2. FIG. 2 is a block diagram illustrating an example of the configuration of the network model integration system 10 to which the present embodiment is applied, and only portions of the configuration associated with the present embodiment are shown conceptually. In the present embodiment, a standalone-type network model integration system 10 (a network model integration device 100) is explained as a specific example. However, the present invention is not limited to this example but can be applied to a communication-type network model integration system 10 or the like illustrated in FIG. 3 in which a network model integration device 100, single or plural terminal devices 130 (for example, user terminals or the like), single or plural external devices 150 (for example, external databases or the like) are communicably connected. FIG. 3 is a conceptual diagram illustrating an example of an overall configuration of the network model integration system 10 according to the present embodiment. As illustrated in FIG. 3, examples of communication include remote communication such as wired or wireless communication via a network (communication line) 300. These respective units of the network model integration system 10 are communicably connected via an optional communication path. In the present embodiment, the communication-type network model integration system 10 according to the present embodiment may be configured to be functionally or physically distributed or integrated in optional units in such a range that the same advantages and functions as the standalone-type network model integration system 10 are obtained.

In FIG. 2, the network model integration device 100 schematically includes an input unit 112, a display unit 114, a control unit 102, and a storage unit 106. The control unit 102 is a CPU or the like that controls the entire network model integration device 100 as a whole. The storage unit 106 is a device that stores various databases, tables, and the like. These respective units of the network model integration device are communicably connected via an optional communication path. Further, the network model integration device 100 may be communicably connected to the network (communication line) 300 via a communication device such as a router and a wired or wireless communication line such as a private line. The input unit 112 may be an inputting unit (for example, a key input unit, a touch panel, a keyboard, a microphone, and the like) for inputting data, a selection instruction, and the like. The display unit 114 is a display unit (for example, a display, a monitor, and the like formed of liquid crystals or organic EL) for displaying a display screen of an application or the like. An input/output control interface unit 108 controls the input unit 112, the display unit 114, and the like.

The databases and tables (a network model database 106a, an interaction database 106b, a pathway database 106c, a literature information database 106d, a news database 106e, a text mining database 106f, and an advertisement information database 106g) stored in the storage unit 106 are stationary disk devices such as a hard disk drive (HDD) and storage units such as a solid state drive (SSD). For example, the storage unit 106 stores various programs, tables, files, databases, web pages, and the like used in various processes.

Among the respective constituent elements of the storage unit 106, the network model database 106a is a network model storage unit that stores a network model that includes nodes that represent constituent elements of a biological object and edges (arcs) that represent interactions between the constituent elements and an network model ID that identifies the network model in association. The network model database 106a may further store notes for a portion or all of network models, nodes, or notes in association with the portion or all of the network models, the nodes, or the edges. Here, the notes may be tags, comments, threads, or the like. The network model database 106a may further store evaluation values on retrieval results that includes edges retrieved by the control unit 102 and network model IDs that identify the network models including the edges in association with the edges included in the retrieval results. Further, the constituent elements of the biological object may be atoms (for example, a hydrogen atom, an oxygen atom, a carbon atom, or a nitrogen atom), ions (for example, a sodium ion, a potassium ion, or a calcium ion), molecules (for example, amino acids, proteins, sugars, lipids, DNA, RNA, or enzymes), cells, tissues, organs, or the like. Furthermore, the network model may be a model that includes at least one constituent element.

The interaction database 106b is an interaction storage unit that stores a list in which the nodes that represent constituent elements and the edges that represent interactions between the constituent elements, the nodes and edges being included in the network model stored in the network model database 106a are associated with a network model ID that identifies the network model. The list stored in the interaction database 106b may be generated based on the nodes, the edges, and the network model ID extracted from the network model database 106a by the control unit 102.

The pathway database 106c is a pathway storage unit that stores a pathway of the constituent elements of the biological object. Here, the pathway may be a metabolic pathway, a signal transduction pathway, or the like within a biological object.

The literature information database 106d is a literature information storage unit that stores literature information on literatures regarding the constituent elements of a biological object and interactions of the constituent elements. The literature information database 106d may store literature information (literature related data) possessed by publishers or the like. These items of literature information may be stored in advance in the literature information database 106d, and the control unit 102 of the network model integration device 100 may periodically download the latest data issued sequentially in the world via the network (communication line) 300 from an external machine (for example, a literature information providing service or the like that provides literature information of publishers, government organizations, and the like) and update the literature information stored in the literature information database 106d.

The news database 106e is a news storage unit that stores the news provided by a news delivery service. The news is information related to the constituent elements of a biological object and interactions between the constituent elements and may be usefulness data or the like on the pathways of new medicines issued by pharmaceuticals, for example.

The text mining database 106f is a text mining storage unit that stores text information related to the constituent elements and interactions that are extracted from the literature information using text mining. The text mining database 106f may further store text information related to the constituent elements and interactions that are extracted from various items of information present on the Internet using text mining.

The advertisement information database 106g is an advertisement information storage unit that stores advertisement information related to the constituent elements of a biological object and the interactions between the constituent elements.

In FIG. 2, the control unit 102 includes an internal memory for storing a control program such as an operating system (OS), a program that defines various processing procedures, and necessary data. The control unit 102 performs information processing for executing various processes using these programs. The control unit 102 conceptually includes, as its functional units, a retrieving unit 102a, a retrieval result displaying unit 102b, an integrating unit 102c, a network model storing unit 102d, a configuration notifying unit 102e, a note storing unit 102f, a note notifying unit 102g, an evaluation value storing unit 102h, a keyword acquiring unit 102i, a literature information retrieving unit 102j, a literature information displaying unit 102k, a literature information notifying unit 102m, an advertisement information acquiring unit 102n, an advertisement information displaying unit 102p, a network model displaying unit 102q, and a literature model acquiring unit 102r.

Among these units, the retrieving unit 102a is a retrieving unit that, when a network model is designated by the user via the input unit 112, retrieves edges that do not constitute a designated network model which is the network model and are stored in the network model database 106a or the interaction database 106b and are linked to the nodes that constitute the designated network model. The retrieving unit 102a may further retrieve edges that do not constitute the designated network model and are linked to the nodes that constitute the designated network model from any one or all of the pathways stored in the pathway database 106c, the literature information stored in the literature information database 106d, the news stored in the news database 106e and/or the text information stored in the text mining database 106f, and may acquire a network model ID that identifies the network model that includes the edges. The retrieving unit 102a may retrieve the edges stored in the network model database 106a or the interaction database 106b that is designated in advance by the user via the input unit 112. Moreover, the designated network model may be a network model stored in the network model database 106a, an existing network model (for example, a network model provided via a web service) that is not stored in the network model database 106a, or a new network model. The retrieving unit 102a may further retrieve edges that do not constitute the designated network model and are linked to the nodes that constitute the designated network model from various information sources on the Internet and acquire a network model ID that identifies a network model that includes the edges.

The retrieval result displaying unit 102b is a retrieval result displaying unit that displays the retrieval results including the edges retrieved by the retrieving unit 102a and the network model IDs that identify the network models including the edges on the display unit 114 in a selectable manner. The retrieval result displaying unit 102b may further display the retrieval results including the nodes that do not constitute the designated network model and are linked to the edges retrieved by the retrieving unit 102a and network model IDs that identify the network models including the nodes on the display unit 114 in a selectable manner. Further, the retrieval result displaying unit 102b may perform any one or both of a process of displaying the retrieval results on the display unit 114 in a list form in a selectable manner and a process of displaying the retrieval results on the display unit 114 so as to be superimposed on the network model. Furthermore, the retrieval result displaying unit 102b may further display evaluation values on the retrieval results corresponding to the edges retrieved by the retrieving unit 102a on the display unit 114.

The integrating unit 102c is an integrating unit that, when the retrieval results displayed on the display unit 114 by the retrieval result displaying unit 102b are selected by the user via the input unit 112, generates an integrated network model which is a network model in which the edges included in the selected retrieval results and the nodes that do not constitute the designated network model and are linked to the edges are integrated into the designated network model. The integrating unit 102c may automatically select retrieval results based on certain criteria (for example, conditions or the like set in advance by the user) and may generate an integrated network model which is a network model in which the edges included in the selected retrieval results and the nodes that do not constitute the designated network model and are linked to the edges are integrated into the designated network model.

The network model storing unit 102d is a network model storing unit that acquires a network model ID that identifies the integrated network model generated by the integrating unit 102c and stores the integrated network model and the network model ID in the network model database 106a in association. When an existing network model or a new network model is input by the user via the input unit 112, the network model storing unit 102d may further acquire a network model ID that identifies the designated network model and store the designated network model and the network model ID in the network model database 106a in association. When an ID selection instruction is input by the user via the input unit 112, the network model storing unit 102d may acquire the network model ID that identifies the designated network model, included in the integrated network model or a new network model ID as a network model ID that identifies the integrated network model based on the ID selection instruction and may store the integrated network model and the network model ID in the network model database 106a in association. The network model storing unit 102d may further store the network model acquired by the literature model acquiring unit 102r and the network model ID in the network model database 106a in association.

The configuration notifying unit 102e is a configuration notifying unit that, when the edges stored in the network model database 106a or the interaction database 106b are retrieved by the retrieving unit 102a, notifies the user, who has provided the network model, of any one or both of the nodes and edges that are included in the designated network model and are not included in the network model stored in the network model database 106a identified by the network model ID corresponding to the edges. When the integrated network model is generated by the integrating unit 102c, the configuration notifying unit 102e may notify the user, who has provided the network model, of any one or both of the nodes and edges that are included in the integrated network model and are not included in the network model stored in the network model database 106a identified by the network model ID corresponding to the edges that are included in the retrieval results selected by the user via the input unit 112.

The note storing unit 102f is a note storing unit that, when notes are input by the user via the input unit 112 with respect to a portion or all of the network models, the nodes included in the network model, or the edges included in the network model, stored in the network model database 106a, stores the notes in the network model database 106a in association with the portion or all of the network models, the nodes, or the edges.

The note notifying unit 102g is a note notifying unit that notifies the user, who has provided the network model corresponding to the notes, the network model that includes the nodes corresponding to the notes, or the network model that includes the edges corresponding to the notes, of the notes stored in the network model database 106a.

The evaluation value storing unit 102h is an evaluation value storing unit that, when evaluation values on the retrieval results are input by the user via the input unit 112, stores the evaluation values in the network model database 106a in association with the edges included in the retrieval results. The evaluation values may be input when the retrieval results displayed on the display unit 114 by the retrieval result displaying unit 102b are selected.

The keyword acquiring unit 102i is a keyword acquiring unit that, when a portion or all of the network models, the nodes, or the edges are selected by the user via the input unit 112, acquires keywords related to the portion or all of the network models, the nodes, or the edges.

The literature information retrieving unit 102j is a literature information retrieving unit that retrieves literature information of literatures issued within a predetermined period, stored in the literature information database 106d using the keywords acquired by the keyword acquiring unit 102*i* at intervals that are set by the user via the input unit 112.

The literature information displaying unit 102*k* is a literature information displaying unit that performs any one or both of a process of displaying the literature information retrieved by the literature information retrieving unit 102*j* on the display unit 114 in a list form and a process of displaying the literature information on the display unit 114 so as to be superimposed on the network model. The literature information displaying unit 102*k* may perform any one or both of the process of displaying the literature information on the display unit 114 in a list form and the process of displaying the literature information on the display unit 114 so as to be superimposed on the network model based on display preference conditions that are set by the user via the input unit 112. The display preference conditions may be literature names, literature issuing organization names, or book titles.

The literature information notifying unit 102*m* is a literature information notifying unit that notifies the user of the literature information retrieved by the literature information retrieving unit 102*j*.

The advertisement information acquiring unit 102*n* is an advertisement information acquiring unit that, when a portion or all of the network models, the nodes, or the edges are selected by the user via the input unit 112, acquires advertisement information stored in the advertisement information database 106*g*, related to the constituent elements or interactions that are based on the portion or all of the network models, the nodes, or the edges. The advertisement information acquiring unit 102*n* may further acquire advertisement information stored in the advertisement information database 106*g*, related to neighboring constituent elements that interact with the constituent elements that are based on the portion or all of the network models, the nodes, or the edges that are selected by the user via the input unit 112. Further, the advertisement information acquiring unit 102*n* may recognize a portion of a network model, which is displayed at the center of the screen for the longest period within a predetermined period, with the aid of the control unit 102, and acquire advertisement information stored in the advertisement information database 106*g*, related to any one or both of the constituent elements based on the nodes and the interactions based on the edges, included in the portion of the network models.

The advertisement information displaying unit 102*p* is an advertisement information displaying unit that displays the advertisement information acquired by the advertisement information acquiring unit 102*n* on the display unit 114.

The network model displaying unit 102*q* is a network model displaying unit that displays network models on the display unit 114. The network model displaying unit 102*q* may further display the notes corresponding to the network models on the display unit 114.

The literature model acquiring unit 102*r* is a literature model acquiring unit that acquires network models from the literature information in which edges are retrieved by the retrieving unit 102*a* using natural language analysis and acquires network model IDs that identify the network models.

Hereinabove, an example of the configuration of the network model integration system 10 according to the present embodiment has been explained.

Process of Network Model Integration System 10

Next, an example of the process of the system according to the present embodiment having such a configuration will be explained in detail with reference to FIGS. 4 to 10.

Process of Standalone-type Network Model Integration System 10

Figure 4:
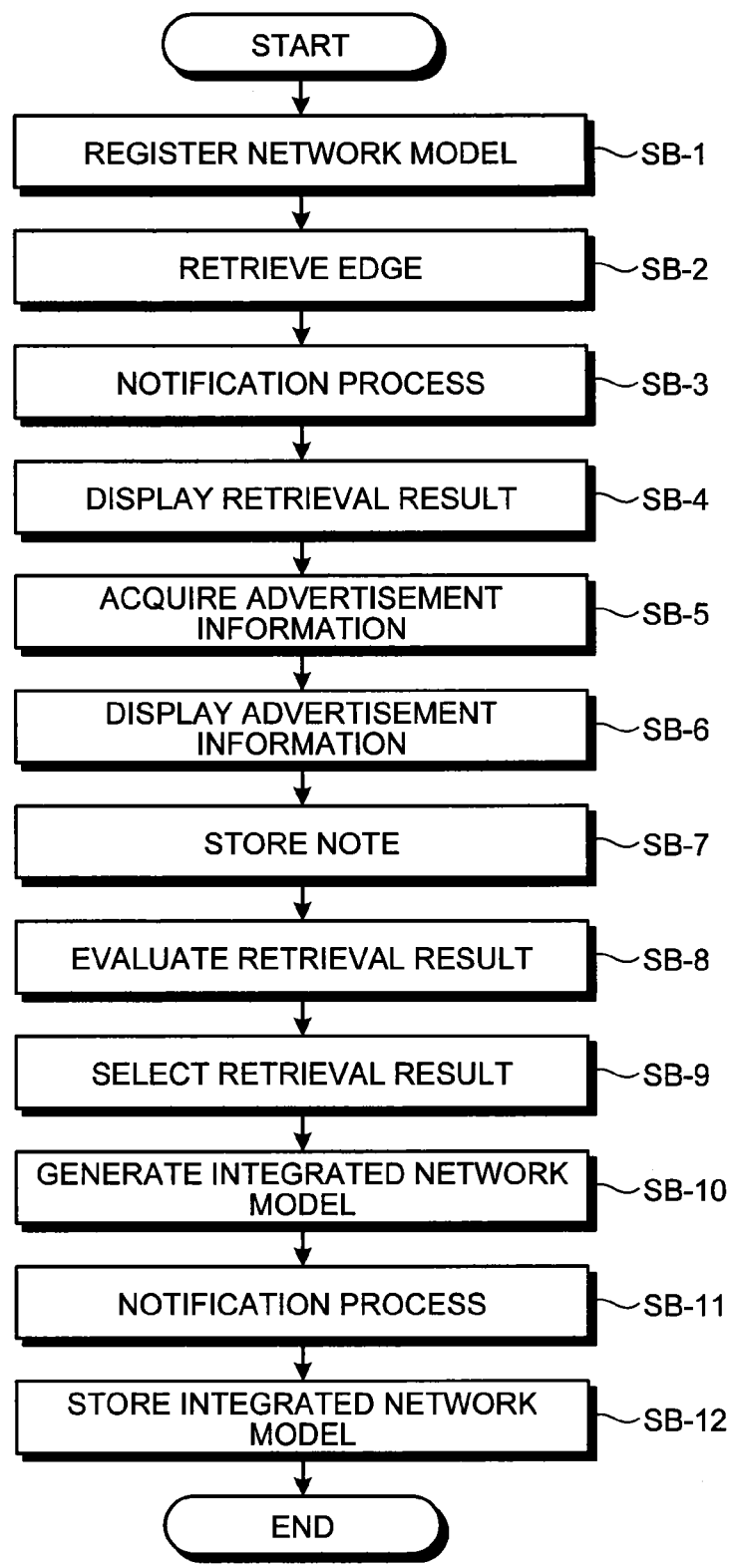
FIG. 4 is a flowchart illustrating an example of the process of the network model integration system 10 according to the present embodiment.

First, the details of the process of the standalone-type network model integration system 10 (the network model integration device 100) according to the present embodiment will be explained with reference to FIGS. 4 to 10. FIG. 4 is a flowchart illustrating an example of the process of the network model integration system 10 according to the present embodiment.

As illustrated in FIG. 4, when a new network model (for example, a network model or the like identified by the user through experiments) is input by the user via the input unit 112, the network model storing unit 102*d* acquires a network model ID that identifies the network model, stores (registers) the network model and the network model ID in the network model database 106*a* in association, and sets the network model as the designated network model of the user (step SB-1). The control unit 102 stores (registers) the nodes and edges included in the network model registered by the network model storing unit 102*d* and the network model ID that identifies the network model in the interaction database 106*b* in association in a list form.

The retrieving unit 102*a* retrieves edges that are stored in the interaction database 106*b*, do not constitute the designated network model, and are linked to the nodes that constitute the designated network model set by the network model storing unit 102*d* (step SB-2). The retrieving unit 102*a* may further retrieve edges that do not constitute the designated network model and are linked to the nodes that constitute the designated network model from any one or all of the pathways stored in the pathway database 106*c*, the literature information stored in the literature information database 106*d*, news stored in the news database 106*e*, the text information stored in the text mining database 106*f*, and various information sources on the Internet and acquire a network model ID that identifies the network model that includes the edges. The retrieving unit 102*a* may retrieve the edges stored in the interaction database 106*b* that is designated in advance by the user via the input unit 112. That is, the retrieving unit 102*a* may selectively retrieve interactions from all items of data on the interaction database 106*b* or designate a target specific network model (which may be singular or plural) to retrieve only the information extracted from the network model (which may be singular or plural). As a result, only the information extracted from a network model that has reliable quality can be used as a retrieval target.

The literature model acquiring unit 102*r* may acquire network models from the literature information in which edges are retrieved by the retrieving unit 102*a* using natural language analysis and acquires network model IDs that identify the network models. The network model storing unit 102*d* may store the network models retrieved by the literature model acquiring unit 102*r* and the network model IDs in the network model database 106*a* in association. That is, in this system, when a reference paper is presented (retrieved) by the retrieving unit 102*a*, the summary of the paper may be extracted in a network form by the literature model acquiring unit 102*r* using a natural language analysis system, and the summary may be stored in the database (the network model database 106*a*) of the network model integration system 10 by the network model storing unit 102*d*. When the user issues a request to display the summary of the paper stored in the network model database 106*a*, a network model related to the interactions stored in the network model database 106*a* may be displayed. The network models extracted from different papers can be treated equally with the network models registered by other users. Thus, by using an arbitration function between a network model corresponding to a certain paper and a network model generated from another paper, a difference between the network models generated from both papers may be displayed. At the same time, interactions based on both papers may be integrated to establish a new network model. Further, the users such as publishers may directly or indirectly use the network model (that is, the summary described herein) acquired according to the present embodiment in relation to the paper issued by the users (publishers).

The user may selectively retrieve information from the interaction database 106b only or may use the other information sources and if used, the user may select which information source will be used. That is, the retrieving unit 102a may retrieve interactions and constituent elements that are already registered in the interaction database 106b and are not reflected on a new network model (designated network model) that is registered in the network model database 106a. At the same time, the retrieving unit 102a may retrieve candidates for the interactions and constituent elements from the text mining database 106f (text mining system), the pathway database 106c, various information sources on the Internet, and the like. That is, the retrieving unit 102a may use external information other than the interaction database 106b and may access external resources such as information on the Internet and commercial databases to extract information from the resources according to an optional method to obtain results.

Figure 5:
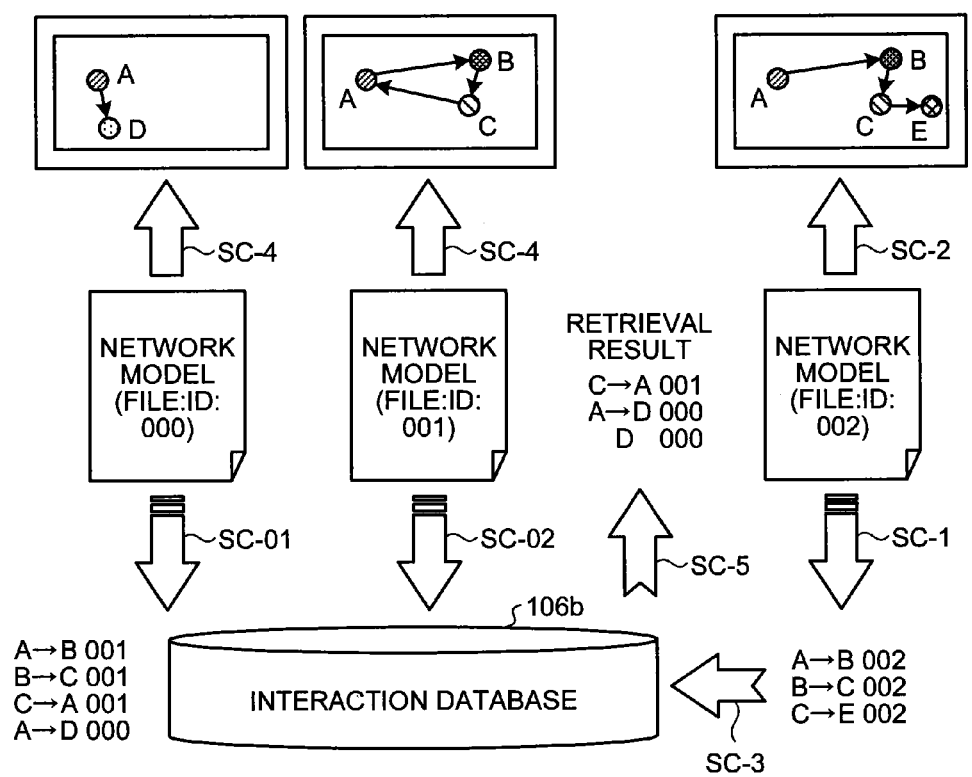
FIG. 5 is a conceptual diagram illustrating an example of the edge retrieving process according to the present embodiment.

An example of an edge retrieving process according to the present embodiment will be explained with reference to FIG. 5. FIG. 5 is a conceptual diagram illustrating an example of the edge retrieving process according to the present embodiment.

As illustrated in FIG. 5, the retrieving unit 102a extracts edges (AB, BC, and CE) that constitute a designated network model (file:ID:002) that is designated by the user via the input unit 112 (step SC-1). As illustrated in FIG. 5, the network model displaying unit 102q may display the designated network model on the display unit 114 (step SC-2). The retrieving unit 102a retrieves, from the interaction database 106b, edges that do not constitute the designated network model and are linked to the nodes (A, B, C, and E) that constitute the extracted designated network model (step SC-3). As illustrated in FIG. 5, the network model displaying unit 102q may display, on the display unit 114, a network model that is stored in the network model database 106a, identified by the network model IDs (file: ID:000 and file:ID:001) corresponding to the retrieval target edges, stored in the interaction database 106b (step SC-4). The retrieving unit 102a acquires the edges (CA and AD) and the node (D) that are stored in the interaction database 106b, do not constitute the designated network model, and are linked to the nodes (A, B, C, and E) that constitute the extracted designated network model as retrieval results (step SC-5). In this manner, in FIG. 5, only the interaction database 106b is a retrieval target, the edges (interactions) that are not included in the designated network model are retrieved from the nodes (constituent elements) that are included in the designated network model, and the edges (interactions) and the nodes (constituent elements) to which the edges (interactions) are linked are obtained as retrieval results. Steps SC-01 and SC-02 illustrated in FIG. 5 will be described later.

Returning to FIG. 4, when the edges stored in the interaction database 106b are retrieved by the retrieving unit 102a, the configuration notifying unit 102e notifies the user, who has provided the network model, of any one or both of the nodes and edges that are included in the designated network model and are not included in the network model stored in the network model database 106a identified by the network model ID corresponding to the edges (step SB-3). Here, the notification may be realized by transmission of emails to users or storing of data including any one or both of the nodes and edges to a user's unique access area within the network model integration device 100.

Figure 6:
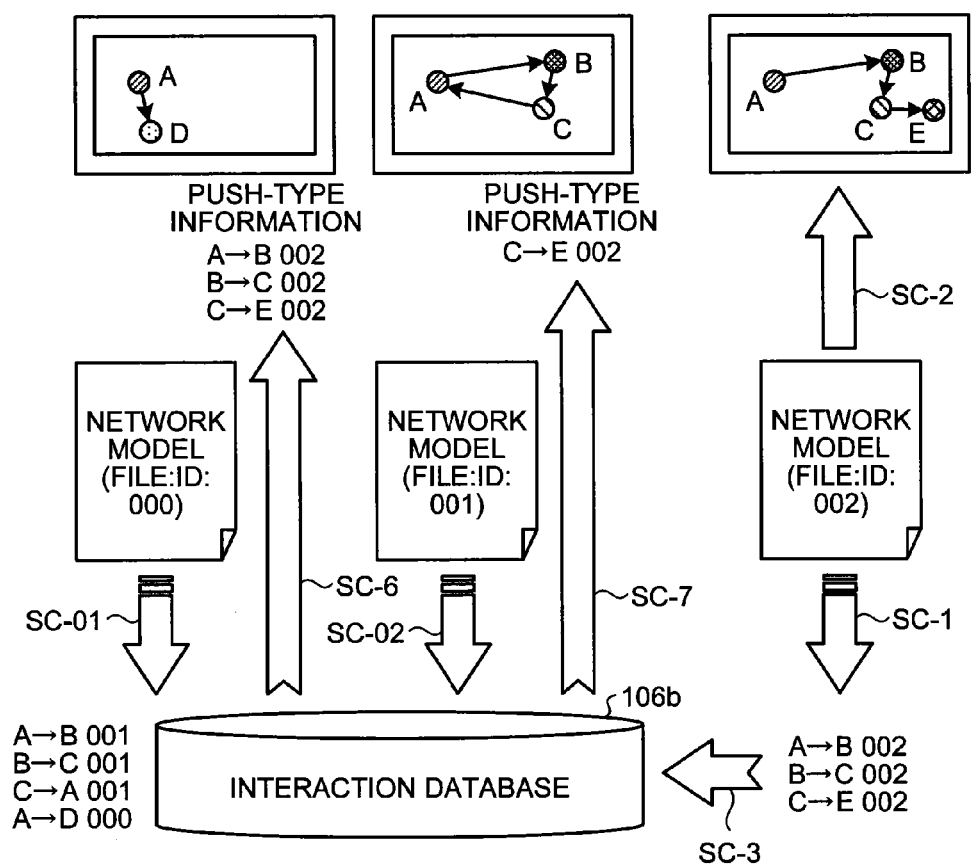
FIG. 6 is a conceptual diagram illustrating an example of the retrieval notification process according to the present embodiment.

An example of a retrieval notification process according to the present embodiment will be explained with reference to FIG. 6. FIG. 6 is a conceptual diagram illustrating an example of the retrieval notification process according to the present embodiment.

As illustrated in FIG. 6, when the edges stored in the interaction database 106b are retrieved by the retrieving unit 102a (step SC-3), the configuration notifying unit 102e notifies the user, who has provided the network model (step SC-01), of the edges (AB, BC, and CE) that are included in the designated network model and are not included in the network model stored in the network model database 106a, identified by the network model ID (file:ID:000) corresponding to the edges. The configuration notifying unit 102e notifies the user, who has provided the network model (step SC-02), of the edge (CE) that is included in the designated network model and is not included in the network model stored in the network model database 106a, identified by the network model ID (file:ID:001) corresponding to the edges (step SC-7). In this manner, the registered network models serve as arbitration targets, and when the edges (interactions) serving as the retrieval keys are not included in the registered network models, the configuration notifying unit 102e notifies the persons or the like, who have registered the network models, of the edges (interactions) serving as the retrieval keys. The processes of steps SC-1 and SC-2 illustrated in FIG. 6 are the same as those of FIG. 5, and explanation thereof will not be provided.

Returning to FIG. 4, the retrieval result displaying unit 102b performs any one or both of a process of displaying, on the display unit 114, the retrieval results including the edges retrieved by the retrieving unit 102a and the network model ID that identifies the network model that includes the edges, stored in the network model database 106a, in a list form in a selectable manner and a process of displaying the retrieval results on the display unit 114 in a selectable manner so as to be superimposed on the network model that includes the edges included in the retrieval results, stored in the network model database 106a (step SB-4). The retrieval result displaying unit 102b may further display, on the display unit 114, retrieval results including the nodes that do not constitute the designated network model and are linked to the edges retrieved by the retrieving unit 102a and the network model ID that identifies the network model that includes the nodes, stored in the network model database 106a in a selectable manner. The retrieval result displaying unit 102b may further display, on the display unit 114, evaluation values on the retrieval results stored in the network model database 106a, corresponding to the edges retrieved by the retrieving unit 102a. That is, the retrieval result displaying unit 102b may present the retrieval results in any one or both of a list form and such a form that the retrieval results are superimposed on the network model. The retrieval result displaying unit 102b may further display, on the display unit 114, the notes stored in the network model database 106a, corresponding to a portion or all of the network models displayed on the display unit 114, the nodes, or the edges.

Figure 7:
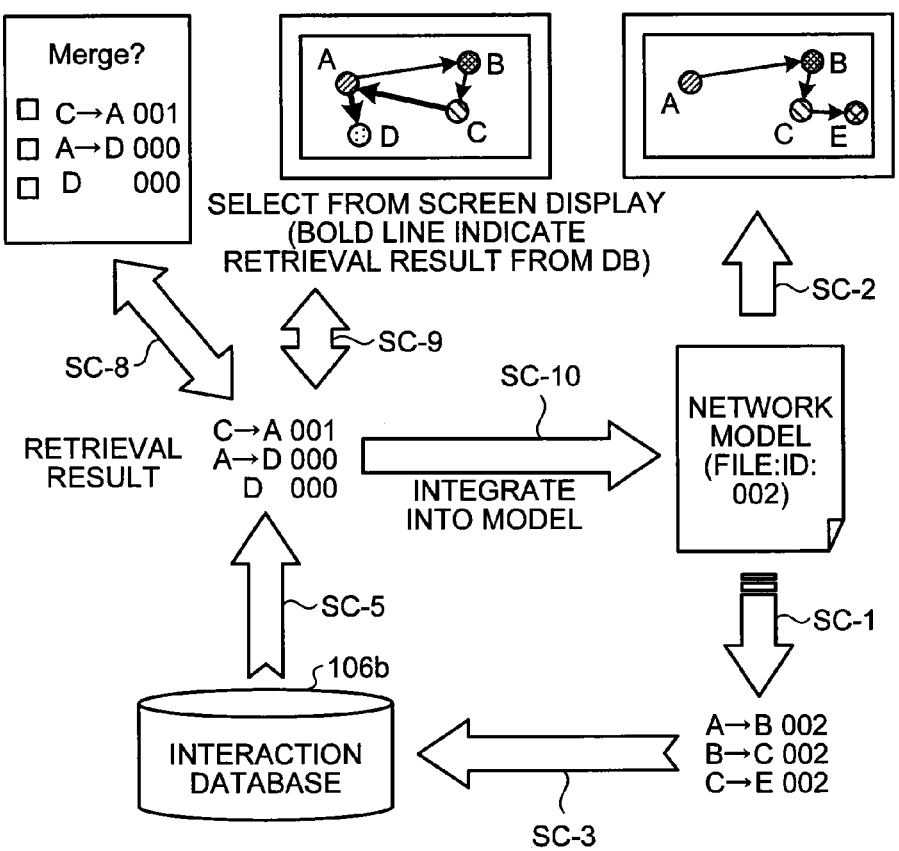
FIG. 7 is a conceptual diagram illustrating an example of the retrieval result displaying process according to the present embodiment.

Next, an example of a retrieval result displaying process according to the present embodiment will be explained with reference to FIG. 7. FIG. 7 is a conceptual diagram illustrating an example of the retrieval result displaying process according to the present embodiment.

As illustrated in FIG. 7, the retrieval result displaying unit 102b displays check boxes next to the retrieval results (step SC-5) acquired by the retrieving unit 102a so that the retrieval results (step SC-5) in the list form can be selected on the display unit 114 (step SC-8). The retrieval result displaying unit 102b displays the retrieval results (step SC-5) acquired by the retrieving unit 102a on the display unit 114 so that selectable arrows (depicted by bold lines) are superimposed on the network model that includes the edges included in the retrieval results (step SC-9). The user may set in advance whether the retrieved interactions and the like will be automatically integrated into the network model or it will be individually determined by the user. When the user determines whether or not to individually integrate the retrieved interactions, the user may individually select whether the respective edges (interactions) and the connection destination nodes (constituent elements) will be integrated into the network model in the displayed list or the display screen of the network model. The processes of steps SC-1, SC-2, and SC-3 illustrated in FIG. 7 are the same as those of FIGS. 5 and 6, and explanation thereof will not be provided.

Returning to FIG. 4, when a portion or all of the network models displayed on the display unit 114 by the retrieval result displaying unit 102b, the nodes, or the edges are selected (for example, by clicking, tapping, or the like) by the user via the input unit 112, the advertisement information acquiring unit 102n acquires advertisement information stored in the advertisement information database 106g, related to the constituent elements or interactions that are based on the portion or all of the network models, the nodes, or the edges (step SB-5). The advertisement information acquiring unit 102n may further acquire advertisement information stored in the advertisement information database 106g, related to neighboring constituent elements that interact with the constituent elements that are based on the portion or all of the network models, the nodes, or the edges that are selected by the user via the input unit 112. Further, the advertisement information acquiring unit 102n may recognize a portion of a network model, which is displayed at the center of the screen of the display unit 114 by the retrieval result displaying unit 102b for the longest period within a predetermined period and acquire advertisement information stored in the advertisement information database 106g, related to the constituent elements based on the nodes and the interactions based on the edges, included in the portion of the network models.

The advertisement information displaying unit 102p displays the advertisement information acquired by the advertisement information acquiring unit 102n on the display unit 114 (step SB-6).

Figure 8:
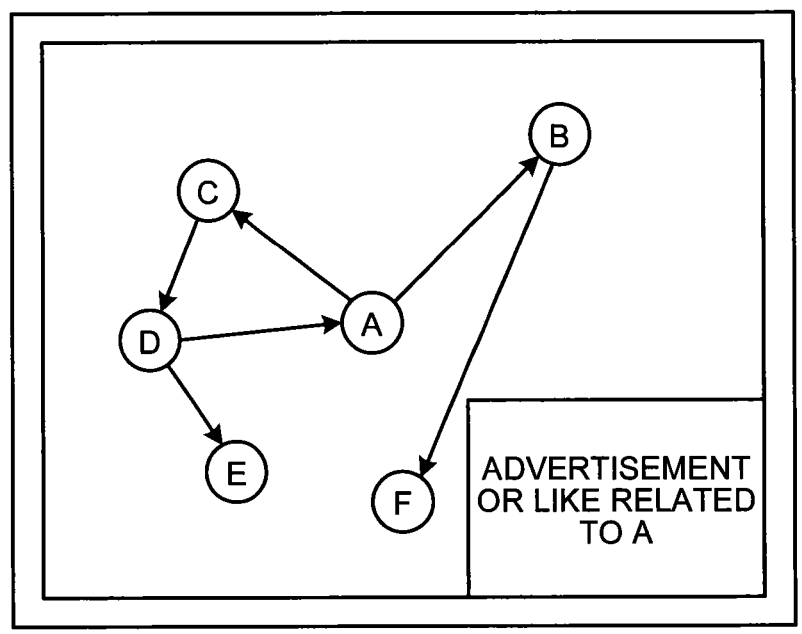
FIG. 8 is a conceptual diagram illustrating an example of the advertisement displaying process according to the present embodiment.

Next, an example of an advertisement displaying process according to the present embodiment will be explained with reference to FIG. 8. FIG. 8 is a conceptual diagram illustrating an example of the advertisement displaying process according to the present embodiment.

As illustrated in FIG. 8, the network model displaying unit 102q graphically displays a network model of intermolecular interactions within a cell on the display unit 114. In this example, since the node A included in the network model that is displayed on the display unit 114 by the network model displaying unit 102q is input by the user via the input unit 112, the advertisement information acquiring unit 102n acquires advertisement information stored in the advertisement information database 106g, related to molecules that are based on the node A. The advertisement information displaying unit 102p displays the advertisement information (advertisements or the like related to the node A) acquired by the advertisement information acquiring unit 102n on the display unit 114.

That is, in the present embodiment, when information related to biology such as an intermolecular interaction network, a transcription control network, an intercellular communication, or an inter-organ interaction is displayed as a network using a program or a service on the Internet, the advertisement information displaying unit 102p can display announcement information such as advertisements or the like prepared in advance on the screen. Further, when the user edits the network model itself displayed on the display unit 114, the user retrieves information on the respective elements (nodes and edges) and regions on the display screen, or the user adds or edits various comments such as tags and threads, the advertisement information displaying unit 102p can display announcement information such as advertisements or the like prepared in advance on the screen. When the network model is displayed graphically on the display unit 114, the user can change (for example, by scrolling, enlarging, reducing, or the like) the content and the display range on the screen according to a method prepared according to this system.

In the present embodiment, the elements (nodes and edges) that constitute the network model stored in the network model database 106a displayed on the display unit 114 may include data used in displaying, singular or plural keywords, link information to related databases, and the like. The advertisement information displaying unit 102p may select and display singular or plural announcements using information on all elements (nodes and edges) of the network model that is presently displayed on the display unit 114, for example. In this case, the advertisement information acquiring unit 102n may compare the keywords for all elements that are always displayed on the screen with the content of announcements and registered keywords that are registered in advance in the advertisement information database 106g and acquire one or plural announcements (advertisements) having the highest relevance. The advertisement information displaying unit 102p may display announcement in one or plural display regions that are prepared in advance. Moreover, a person who wants to place advertisements may add a series of advertisements related to a network model registered to the account of the user to the network model possessed by the person using a push-type information transfer method and register the advertisements in this system. In this case, in addition to displaying advertisements on the screen displayed by the user using a push-type information transfer mechanism that is defined in advance, the advertisement information displaying unit 102p may manage the displaying of advertisements for each user in such a manner that a "user advertisement list" is displayed for an individual user so that advertisements other than the advertisements that have been read by the user are displayed.

In the conventional technology, when announcements such as advertisements are displayed on an electronic medium such as the Internet, an advertisement or the like that is determined in advance is automatically displayed when the page is displayed. Many retrieval engines use a method of allowing the person who places announcements to register specific keywords and presenting the announcements on the screen when the user uses the keywords in the course of retrieving and the keywords meet specific criteria. However, in biological networks, a large amount of information is presented at a time, and the user retrieves a larger amount of information by selecting an element that is already displayed. Thus, the conventional technology cannot present an appropriate announcement. Moreover, when a network model is displayed, a retrieval keyword used for displaying the network model is a file name thereof, the name of an entire pathway, or the like, but it is not always the case that the names of specific genes, proteins, and the like in which the user is interested are used. However, in many cases, since the user adjusts the screen display so that an interesting element is disposed near the center of the screen, it is natural to think that the user is most interested in the interaction and constituent element that are displayed near the center of the screen.

Therefore, in the present embodiment, the advertisement information acquiring unit 102n may compute the form (topology) of a network formed by the nodes and edges included in the network model that is displayed at the center of the screen of the display unit 114 for the longest period within a predetermined period or the period in which the network model is displayed near the center of the screen and set the computed value as an interest scale of the user. The advertisement information acquiring unit 102n may acquire advertisement information stored in the advertisement information database 106g, related to the network model displayed on the display unit 114 based on the set interest scale. The advertisement information displaying unit 102p may display the advertisement information acquired by the advertisement information acquiring unit 102n on the display unit 114. That is, the advertisement information displaying unit 102p displays the interaction and the constituent elements that are displayed near the center of the screen for the longest period, the topology thereof, or advertisements related to biological functions and the like by determining whether to display the same, the display order, the positions, and the like based on the features that are designated in advance by an information provider such as an advertiser.

Returning to FIG. 4, when notes are input by the user via the input unit 112 with respect to a portion or all of the network models displayed on the display unit 114 by the retrieval result displaying unit 102b, the nods included in the network model, or the edges included in the network model, the note storing unit 102f stores the notes in the network model database 106a in association with the portion or all of the network models, the nodes, or the edges (step SB-7). The retrieval result displaying unit 102b may display the notes stored in the network model database 106a by the note storing unit 102f on the display unit 114 so as to be superimposed on the portion or all of the network models, the nodes, or the edges. That is, in the present embodiment, a network model registered (uploaded) to the network model database 106a by network model providers (for example, researchers, publishers, advertisers, and the like) is displayed on the display unit 114 according to retrieval of users and the like, and the user can set tags, comments, threads, or the like to the regions, constituent elements, interactions, or the like of the displayed network model.

The note notifying unit 102g may notify the user (provider), who has provided a network model corresponding to the notes, a network model that includes the nodes corresponding to the notes, or a network model that includes the edges corresponding to the notes which is stored in the network model database 106a, of the notes stored in the network model database 106a by the note storing unit 102f. That is, when the user adds various comments in the form of tags, threads, or the like to a target network model, the note notifying unit 102g may automatically feed the comments or the like of the user back to the providers who have provided information on the respective network models in an edited or non-edited form. The note notifying unit 102g may notify the providers of the information such as various comments added by the user by arranging the information in such a form that is agreed with the provider for each network model according to a cycle and a filter that are defined in advance.

When evaluation values on the retrieval results are input by the user via the input unit 112, the evaluation value storing unit 102h stores the evaluation values in the network model database 106a in association with the edges included in the retrieval results (step SB-8). The evaluation values may be input when the retrieval results displayed on the display unit 114 by the retrieval result displaying unit 102b are selected. That is, in the present embodiment, the user may evaluate the reliability of the interactions corresponding to the edges included in the retrieval results on literature retrieval, text mining, and various internal and external databases, displayed on the retrieval result displaying unit 102b in terms of numerical values or binary values. The evaluation value storing unit 102h may store the evaluation values in the network model database 106a together with the edges that represent the presented interactions and the retrieval results that include the presented interactions. The integrating unit 102c may integrate the edges that represent the interactions that the evaluation value storing unit 102h has evaluated that the user will add the same to the designated network model into the network model of the user. When an edge that represents one interaction is presented to a plurality of users and evaluated, the evaluation value storing unit 102h may further store the number of users serving as a parameter and the evaluation results in the network model database 106a.

When the retrieval results displayed on the display unit 114 by the retrieval result displaying unit 102b are selected by the user via the input unit 112, the integrating unit 102c detects the selection (step SB-9).

The integrating unit 102c generates an integrated network model which is a network model in which the edges included in the retrieval results selected by the user via the input unit 112 and the nodes that do not constitute the designated network model and are linked to the edges are integrated into the designated network model (step SB-10). The integrating unit 102c may automatically select retrieval results based on certain criteria (for example, conditions or the like set in advance by the user) and generate an integrated network model which is a network model in which the edges included in the selected retrieval results and the nodes that do not constitute the designated network model and are linked to the edges are integrated into the designated network model. Either one of the processes of steps SB-8 and SB-9 may be performed earlier than the other, and both processes may be performed simultaneously. That is, in the present embodiment, the edges that represent the interactions selected by the user via the input unit 112 may be integrated with the network model simultaneously with storing of the evaluation values (user's evaluation) on the retrieval results (interactions) presented from various information sources in the database.

An example of an integration process according to the present embodiment will be explained with reference to FIG. 7.

As illustrated in FIG. 7, the integrating unit 102c integrates the edges (CA and AD) included in the retrieval results that are selected by the user via the input unit 112 and a node (D) that does not constitute the designated network model and is linked to the edges into the designated network model (file: ID:002) (step SC-10).

Returning to FIG. 4, the configuration notifying unit 102e notifies the user, who has provided the network model, of any one or both of the nodes and edges that are included in the integrated network model generated by the integrating unit 102c and are not included in the network model stored in the network model database 106a, identified by the network model ID corresponding to the edges that are included in the retrieval results that are selected by the user via the input unit 112 (step SB-11). That is, in the present embodiment, when the network model is integrated, the items of information on the interactions that are instructed to be integrated and the connection destination constituent elements thereof are stored separately, and the configuration notifying unit 102e sends the items of information to the provider of the network model.

The network model storing unit 102d acquires the network model ID that identifies the integrated network model generated by the integrating unit 102c and stores the integrated network model and the network model ID in the network model database 106a in association (step SB-12). In this way, the process ends. The network model displaying unit 102q may display the integrated network model generated by the integrating unit 102c on the display unit 114 to allow the user to check the integration results. When an ID selection instruction is input by the user via the input unit 112, the network model storing unit 102d may acquire a network model ID that identifies the designated network model included in the integrated network model or a new network model ID as a network model ID that identifies the integrated network model based on the ID selection instruction and store the integrated network model and the network model ID in the network model database 106a in association. That is, the network model storing unit 102d may allow the user to select whether the integrated network model will maintain the original file name and the original network model ID or have a new file name and a new network model ID and register the file name and the network model ID selected by the user.

Figure 9:
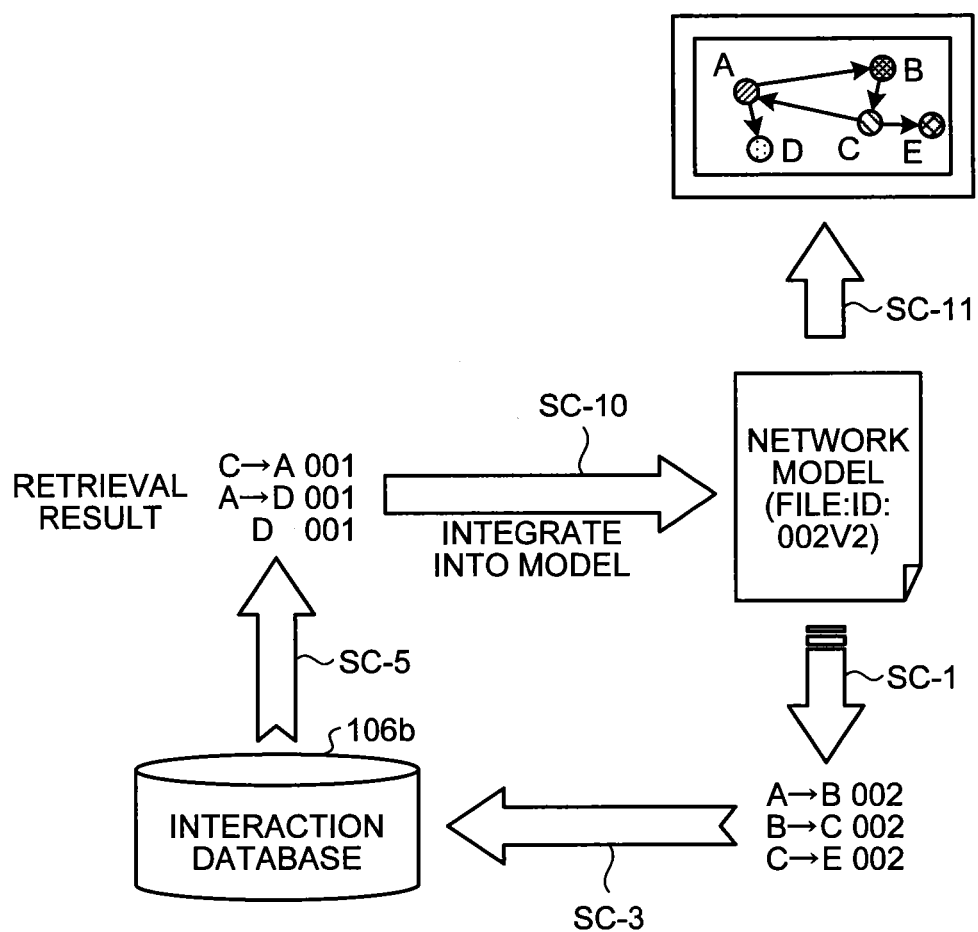
FIG. 9 is a conceptual diagram illustrating an example of the integration process according to the present embodiment.

An example of the integration process according to the present embodiment will be explained with reference to FIG. 9. FIG. 9 is a conceptual diagram illustrating an example of the integration process according to the present embodiment.

As illustrated in FIG. 9, the network model storing unit 102d acquires a new network model ID (file:ID:002v2) that identifies the integrated network model generated by the integrating unit 102c and stores the integrated network model and the new network model ID in the network model database 106a in association. The network model displaying unit 102q displays the integrated network model on the display unit 114 (step SC-11). The processes of steps SC-1, SC-3, SC-5, and SC-10 illustrated in FIG. 9 are the same as those of FIG. 7, and explanation thereof will not be provided.

Hereinabove, an example of the process of the standalone-type network model integration system 10 according to the present embodiment has been explained.

Latest Literature Automatic Displaying Process

Figure 10:
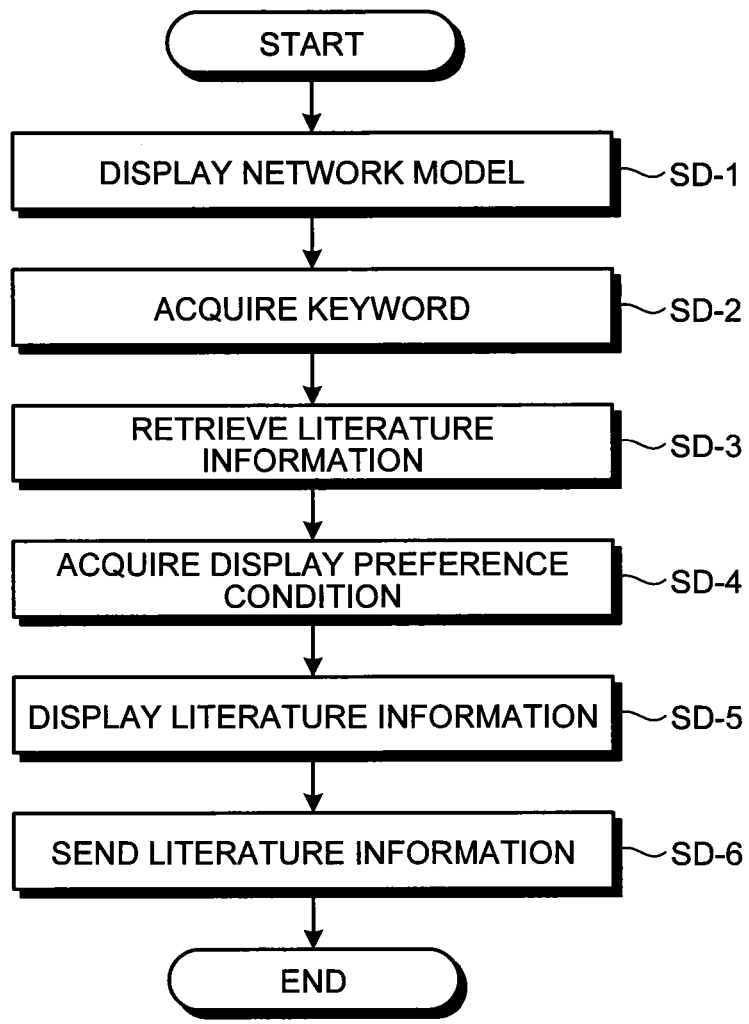
FIG. 10 is a flowchart for explaining an example of the latest literature automatic displaying process according to the present embodiment.

Next, the details of a latest literature automatic displaying process according to the present embodiment will be explained with reference to FIG. 10. FIG. 10 is a flowchart for explaining an example of the latest literature automatic displaying process according to the present embodiment.

As illustrated in FIG. 10, the network model displaying unit 102q displays the network model stored in the network model database 106a on the display unit 114 (step SD-1).

When a portion or all of the network models displayed by the network model displaying unit 102q, the nodes, or the edges are selected by the user via the input unit 112, the keyword acquiring unit 102i acquires keywords related to the portion or all of the network models, the nodes, or the edges (step SD-2).

The literature information retrieving unit 102j retrieves literature information on literatures issued within a predetermined period, stored in the literature information database 106d using the keywords acquired by the keyword acquiring unit 102i at intervals that are set in advance by the user via the input unit 112 (step SD-3). That is, in the present embodiment, the literature information retrieving unit 102j retrieves the literature information database 106d or the like at intervals of time determined in advance using the keywords that are included in one or plural elements and regions on the screen, all displayed networks or screens and are selected by the user in advance and identifies papers that are newly issued within a predetermined period. Further, the literature information retrieving unit 102j may further retrieve the literature information using constraint conditions that are set in advance by the user, other than the keywords acquired by the keyword acquiring unit 102i.

The control unit 102 acquires display preference conditions that are input in advance by the user via the input unit 112 and set (step SD-4). Here, the display preference conditions may be literature names, literature issuing organization names, or book titles.

The literature information displaying unit 102k performs any one or both of a process of displaying the literature information that is retrieved by the literature information retrieving unit 102j and meets the display preference conditions acquired by the control unit 102 on the display unit 114 in a list form and a process of displaying the literature information on the display unit 114 so as to be superimposed on the network model stored in the network model database 106a (step SD-5). That is, in the present embodiment, the literature information displaying unit 102k may generate a tag that is to be displayed in an element or a region which is analyzed to have highest relevance to the titles, the summaries, or the text of the identified papers and display the paper information to be described in the content of the tag. In this case, a plurality of tags may be generated and the information on a plurality of papers may be described in the respective tags. The literature information displaying unit 102k may further create a list of related papers issued within a predetermined period in a predetermined form and display the list on the display unit 114.

The literature information notifying unit 102m notifies the user of the literature information that is retrieved by the literature information retrieving unit 102j and meets the display preference conditions acquired by the control unit 102 (step SD-6). In this way, the process ends. That is, when the user has made notification settings, the literature information notifying unit 102m creates a list of papers retrieved by the literature information retrieving unit 102j and sends the papers to a mail address or the like designated by the user. Either one of the processes of steps SD-5 and SD-6 may be performed earlier than the other, and both processes may be performed simultaneously.

A specific example of the latest literature automatic displaying process will be explained. For example, when the user wants to obtain information on the latest papers related to a MAPK signal transduction system every 24 hours, the user may input settings on the setting screen so that this system retrieves papers issued in the past 24 hours at 6:00 am every morning. Subsequently, the user displays a network model of the MAPK signal transduction system on the screen and selects the most interesting molecule (for example, RAS, RAF, MEK, or ERK). In this case, the literature information retrieving unit 102j extracts, at 6:00 am every morning, papers of which the title or summary includes RAS, RAF, MEK, or ERK from papers that are added to the literature database in the past 24 hours. After that, the literature information displaying unit 102k adds tags in which paper information is described to respective corresponding elements (nodes or edges) on the display screen on which the network model related to the MAPK signal transduction system is displayed. Moreover, when literatures are displayed as an application of a push-type information display function, for example, and the user registers a key network model for the account of the user, the literature information retrieving unit 102*j* acquires a list of papers that the user recognizes in relation to the network model as a "user paper list". After that, the literature information displaying unit 102*k* performs procedures defined by the push-type information display function with respect to the network model and displays information on new nodes and edges together with reference information for papers related to the nodes and edges. Further, by the same procedures, the literature information displaying unit 102*k* may display information on papers that are not present in the user paper list with respect to the nodes and edges that have been displayed already.

Hereinabove, an example of the process of the network model integration system 10 according to the present embodiment has been explained.

First Practical Example

Standalone-type Network Model Integration System 10

Figure 11:
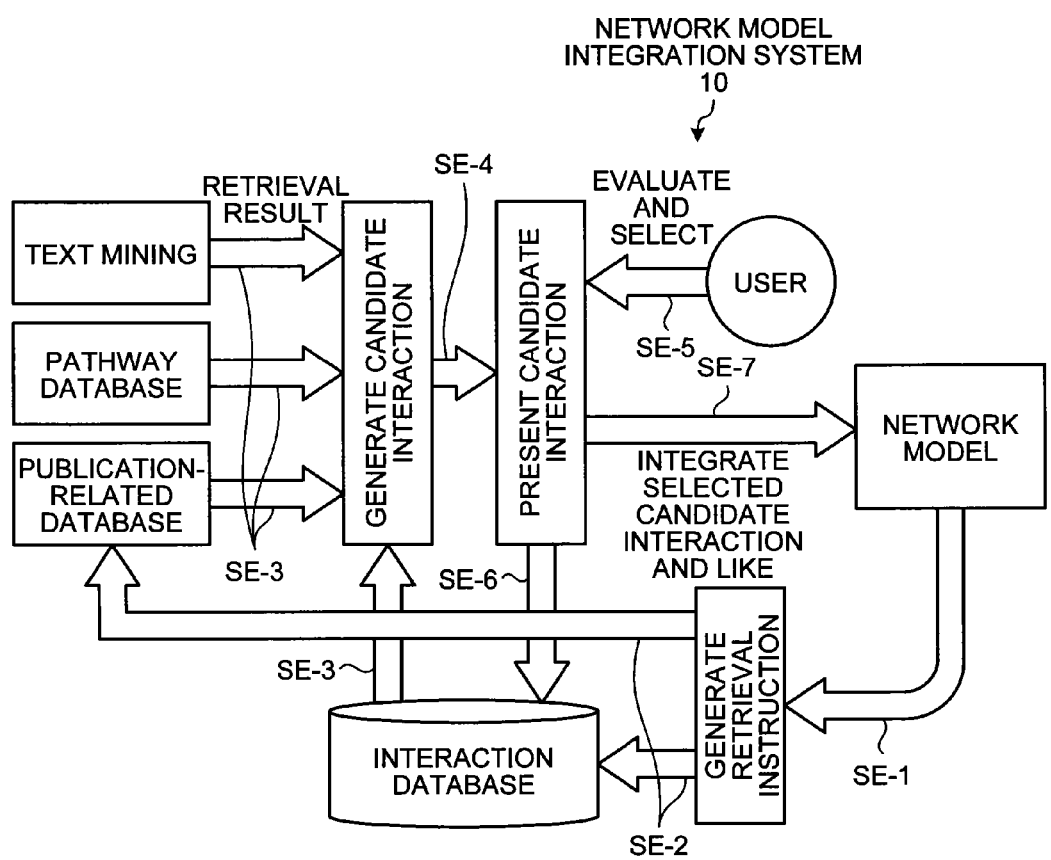
FIG. 11 is a conceptual diagram illustrating an example of the network model integration system 10 according to the present embodiment.

Next, a practical example of the standalone-type network model integration system 10 (the network model integration device 100) according to the present embodiment will be explained with reference to FIG. 11. FIG. 11 is a conceptual diagram illustrating an example of the network model integration system 10 according to the present embodiment.

As illustrated in FIG. 11, the control unit 102 of the network model integration device 100 generates a retrieval instruction to retrieve edges that are linked to the nodes that constitute a network model (designated network model) designated by the user and do not constitute the designated network model (step SE-1).

According to the retrieval instruction, the retrieving unit 102*a* of the network model integration device 100 retrieves edges that are linked to the nodes that constitute the designated network model and do not constitute the designated network model from the edges stored in an interaction database (the interaction database 106*b*), the pathways stored in a pathway database (the pathway database 106*c*), the literature information and news stored in a publication related database (the literature information database 106*d* and the news database 106*e*), and the text information stored in the text mining (text mining database 106*f*) (step SE-2).

The retrieval result displaying unit 102*b* of the network model integration device 100 generates candidate interactions (retrieval results) including the edges retrieved by the retrieving unit 102*a* and the network model ID that identifies the network model that includes the edges (step SE-3).

The retrieval result displaying unit 102*b* of the network model integration device 100 presents the generated candidate interactions (retrieval results) to the user by performing any one or both of a process of displaying the same on the display unit 114 in a list form in a selectable manner and a process of displaying the same on the display unit 114 so as to be superimposed on the network model that includes the edges included in the candidate interactions (retrieval results) in a selectable manner (step SE-4).

When evaluation values on the candidate interactions (retrieval results) are input by the user via the input unit 112 (step SE-5), the evaluation value storing unit 102*h* of the network model integration device 100 stores the evaluation values in the interaction database (any one or both of the network model database 106*a* and the interaction database 106*b*) in association with the edges included in the candidate interactions (retrieval results) (step SE-6).

When the candidate interactions (retrieval results) displayed on the display unit 114 by the retrieval result displaying unit 102*b* are selected by the user via the input unit 112 (step SE-5), the integrating unit 102*c* of the network model integration device 100 generates an integrated network model which is a network model in which the selected interaction or the like (the edges that represent the interactions included in the retrieval results) and the node that does not constitute the designated network model and is linked to the edges are integrated (step SE-7).

Hereinabove, the first practical example according to the present embodiment has been explained.

Second Practical Example

Communication-Type Network Model Integration System 10

Figure 12:
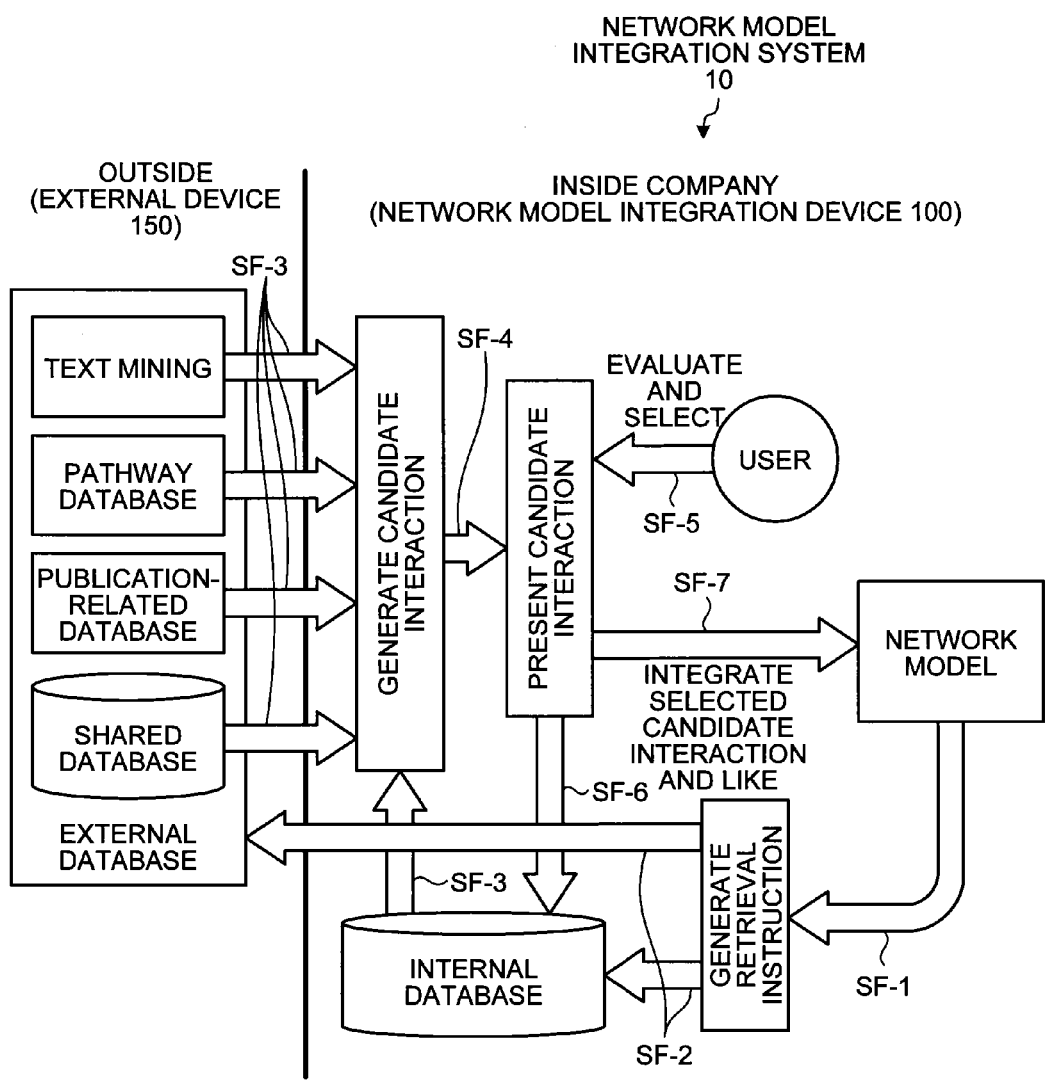
FIG. 12 is a conceptual diagram for explaining an example of the network model integration system 10 according to the present embodiment.

A practical example of the communication-type network model integration system 10 that communicably connects the inside (the network model integration device 100) of a company and the outside (the external device 150 that includes at least a storage unit (a configuration corresponding to the storage unit 106 of the standalone-type network model integration system 10)) according to the present embodiment will be explained with reference to FIG. 12. That is, a practical example of the communication-type network model integration system 10 in which a database (internal database) inside a company and an external database are separated when this system is used in a system or the like within the company will be explained. FIG. 12 is a conceptual diagram for explaining an example of the network model integration system 10 according to the present embodiment.

As illustrated in FIG. 12, the control unit 102 of the network model integration device 100 generates a retrieval instruction to retrieve edges that are linked to the nodes that constitute a network model (designated network model) designated by the user and do not constitute the designated network model (step SF-1).

According to the retrieval instruction, the retrieving unit 102*a* of the network model integration device 100 retrieves edges that are linked to the nodes that constitute the designated network model and do not constitute the designated network model from the edges stored in the internal database (the network model database 106*a* and the interaction database 106*b*) of the network model integration device 100, and the pathways stored in the external databases, that is the pathway database (a configuration corresponding to the pathway database 106*c* of the standalone-type network model integration system 10) of the external device 150, the literature information and news stored in the publication related database (a configuration corresponding to the literature information database 106*d* and the news database 106*e* of the standalone-type network model integration system 10) of the external device 150, the text information stored in the text mining (a configuration corresponding to the text mining database 106*f* of the standalone-type network model integration system 10) of the external device 150, and various items of information stored in a shared database of the external device 150 via the network (communication line) 300 (step SF-2).

The retrieving unit 102*a* of the network model integration device 100 generates candidate interactions (retrieval results) including the retrieved edges and the network model ID that identifies the network model that includes the edges (step SF-3).

The retrieval result displaying unit 102b of the network model integration device 100 presents the candidate interactions (retrieval results) generated by the retrieving unit 102a to the user by performing any one or both of a process of displaying the same on the display unit 114 in a list form in a selectable manner and a process of displaying the same on the display unit 114 so as to be superimposed on the network model that includes the edges included in the candidate interactions (retrieval results) in a selectable manner (step SF-4).

When evaluation values on the candidate interactions (retrieval results) are input by the user via the input unit 112 (step SF-5), the evaluation value storing unit 102h of the network model integration device 100 stores the evaluation values in the internal database (any one or both of the network model database 106a and the interaction database 106b) in association with the edges included in the candidate interactions (retrieval results) (step SF-6).

When the candidate interactions (retrieval results) displayed on the display unit 114 by the retrieval result displaying unit 102b are selected by the user via the input unit 112 (step SF-5), the integrating unit 102c of the network model integration device 100 generates (that is, integrates interactions) an integrated network model which is a network model in which the edges that represent the interaction included in the selected retrieval results and the node that does not constitute the designated network model and is linked to the edges are integrated (step SF-7).

Hereinabove, the second practical example according to the present embodiment has been explained.

Third Practical Example

Communication-Type Network Model Integration System 10

Figure 13:
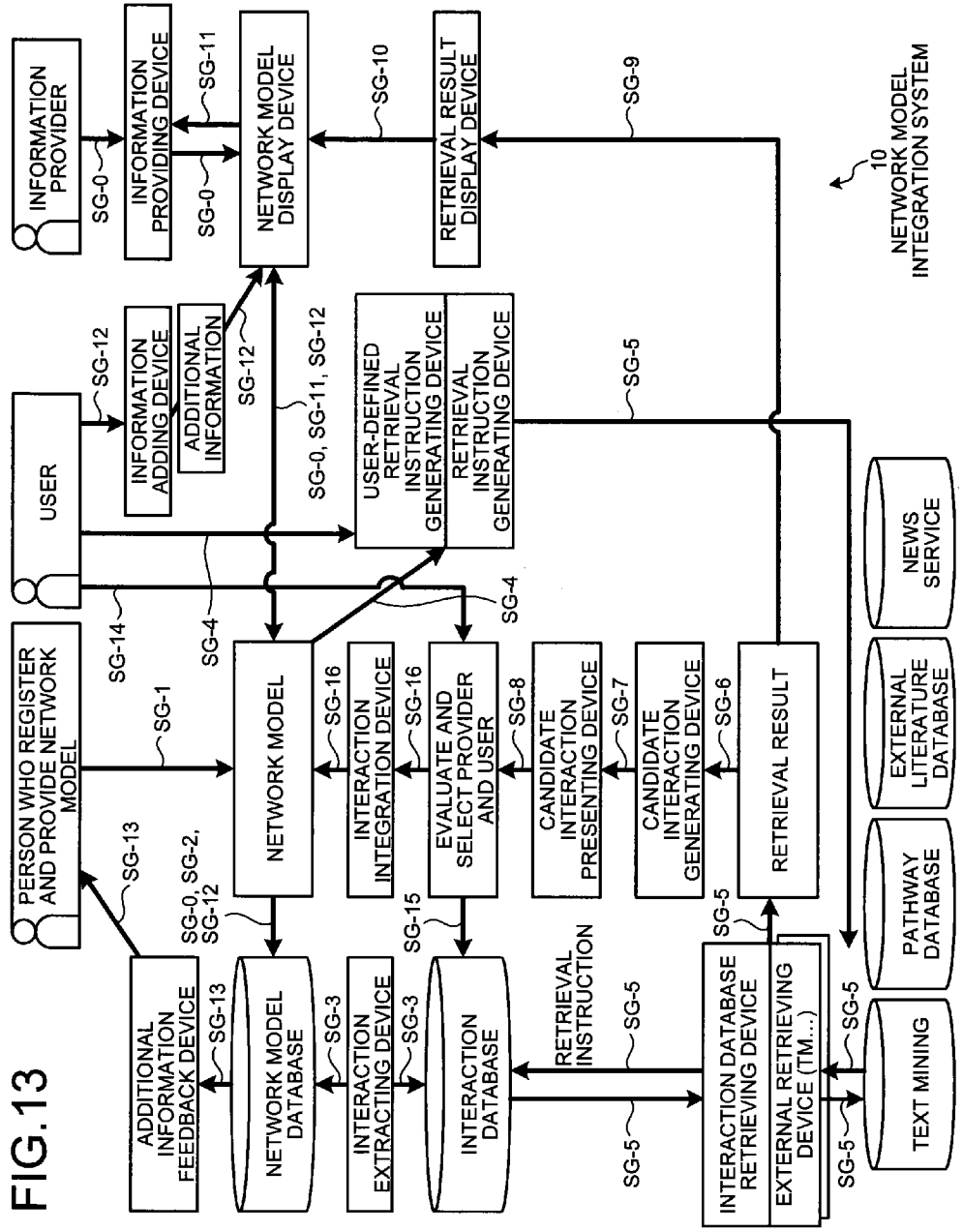
FIG. 13 is a conceptual diagram for explaining an example of the network model integration system 10 according to the present embodiment.

A practical example of the communication-type network model integration system 10 in which the network model integration device 100 that includes at least the control unit 102 and the storage unit 106, the terminal device 130 that includes at least an input unit (a configuration corresponding to the input unit 112 of the standalone-type network model integration system 10) and a display unit (a configuration corresponding to the display unit 114 of the standalone-type network model integration system 10), and the external device 150 that includes at least a storage unit (a configuration corresponding to the storage unit 106 of the standalone-type network model integration system 10) are connected according to the present embodiment will be explained with reference to FIG. 13. FIG. 13 is a conceptual diagram for explaining an example of the network model integration system 10 according to the present embodiment.

As illustrated in FIG. 13, the control unit 102 of the network model integration device 100 receives a new network model that is transmitted from a terminal device 130-1 via the network (communication line) 300 and is input via the input unit of the terminal device 130-1 by a person (the user of the terminal device 130-1) who has registered and provided the network model (step SG-1).

The network model storing unit 102d of the network model integration device 100 acquires the network model ID that identifies the network model received by the control unit 102 and stores (registers) the network model and the network model ID in a network model database (the network model database 106a) in association (step SG-2).

An interaction extracting device (the control unit 102) of the network model integration device 100 stores (registers additionally) the nodes and edges included in the network model that is registered by the network model storing unit 102d and the network model ID that identifies the network model in an interaction database (the interaction database 106b) in association in a list form (step SG-3).

When the network model that is transmitted from a terminal device 130-2 via the network (the communication line) 300 is designated by a user (the user of the terminal device 130-2) via the input unit of the terminal device 130-2, a user-defined retrieval instruction generating device (the control unit 102) of the network model integration device 100 generates a retrieval instruction to retrieve the edges that do not constitute the designated network model and are linked to the nodes that constitute the designated network model which is the network model (step SG-4). When a new network model (designated network model) is received from the terminal device 130-1, a retrieval instruction generating device (the control unit 102) of the network model integration device 100 may generate a retrieval instruction to retrieve the edges that do not constitute the designated network model and are linked to the nodes that constitute the designated network model.

According to the retrieval instruction, an interaction database retrieval device (the retrieving unit 102a) of the network model integration device 100 retrieves the edges that do not constitute the designated network model and are linked to the nodes that constitute the designated network model from the edges stored in an interaction database (the interaction database 106b). Moreover, according to the retrieval instruction, external retrieval devices (the retrieving unit 102a) retrieve the edges from the pathways stored in a pathway database (a configuration corresponding to the pathway database 106c of the standalone-type network model integration system 10) of the external device 150, the literature information stored in an external literature database (a configuration corresponding to the literature information database 106d of the standalone-type network model integration system 10) of the external device 150, the text information stored in the text mining (a configuration corresponding to the text mining database 106f of the standalone-type network model integration system 10) of the external device 150, and the news provided by the news delivery service, stored in a news service (a configuration corresponding to the news database 106e of the standalone-type network model integration system 10) of the external device 150 via the network (the communication line) 300 and generate retrieval results including the retrieved edges and the network model ID that identifies the network model that includes the edges (step SG-5).

A candidate interaction generating device (a configuration corresponding to the retrieval result displaying unit 102b of the standalone-type network model integration system 10) of the terminal device 130-2 receives the retrieval results transmitted from the network model integration device 100 via the network (the communication line) 300 (step SG-6). The candidate interaction generating device of the terminal device 130-2 generates any one or both of a display screen in which the retrieval results are displayed in a list form and a display screen in which the retrieval results are superimposed on a network model that includes the edges included in the retrieval results (step SG-7). A candidate interaction presenting device (a configuration corresponding to the retrieval result displaying unit 102b of the standalone-type network model integration system 10) of the terminal device 130-2 displays the display screen generated by the candidate interaction generating device on the display unit so that the retrieval results can be selected (step SG-8).

When the edges are retrieved by the interaction database retrieval device, an information providing device (the configuration notifying unit 102e) of the network model integration device 100 notifies an information provider (the user of a terminal device 130-3), who has provided in advance the network model (step SG-0), of any one of both of the nodes and edges that are included in the designated network model and are not included in the network model stored in the network model database, identified by the network model ID corresponding to the edges (step SG-9).

A retrieval result displaying device (a configuration corresponding to the retrieval result displaying unit 102*b* of the standalone-type network model integration system 10) of the terminal device 130-3 displays any one or both of the nodes and edges notified from the network model integration device 100 on the display unit in a list form (step SG-10). Further, a network model display device (a configuration corresponding to the retrieval result displaying unit 102*b* of the standalone-type network model integration system 10) of the terminal device 130-3 displays any one or both of the nodes and edges on the display unit so as to be superimposed on the network model that has been provided (step SG-0) by the information provider (the user of the terminal device 130-3) (step SG-11).

When additional information (notes) is input by a user (the user of the terminal device 130-2) via the input unit of the terminal device 130-2 with respect to a portion or all of the network models displayed on the display unit of the terminal device 130-2 by the candidate interaction presenting device of the terminal device 130-2, the nodes included in the network model, or the edges included in the network model, an information adding device (the note storing unit 102*f*) of the network model integration device 100 stores the additional information (notes) in a network model database in association with the portion or all of the network models, the nodes, or the edges (step SG-12).

An additional information feedback device (the note notifying unit 102*g*) of the network model integration device 100 notifies the person (the user of the terminal device 130-1), who has registered and provided the network model corresponding to the additional information (notes), the network model that includes the nodes corresponding to the additional information (notes), or the network model that includes the edges corresponding to the additional information (notes), stored in the network model database, of the additional information (notes) that is stored in the network model database by the information adding device (step SG-13).

When evaluation values on the candidate interactions (retrieval results) that are transmitted from the terminal device 130-2 via the network (the communication line) 300 are input via the input unit of the terminal device 130-2 by a user (the user of the terminal device 130-2) (step SG-14), the evaluation value storing unit 102*h* of the network model integration device 100 stores the evaluation values in an interaction database (the interaction database 106*b*) in association with the edges included in the candidate interactions (retrieval results) (step SG-15).

When the candidate interactions (retrieval results) that are transmitted from the terminal device 130-2 via the network (the communication line) 300 and displayed on the display unit by the candidate interaction presenting device are selected by a user (the user of the terminal device 130-2) via the input unit of the terminal device 130-2 (step SG-14), an interaction integration device (the integrating unit 102*c*) of the network model integration device 100 generates an integrated network model which is a network model in which the edges that represent the interactions included in the selected retrieval results and the nodes that are linked to the edges and do not constitute the designated network model are integrated (step SG-16).

Hereinabove, the third practical example according to the present embodiment has been explained.

Other Embodiments

The embodiment of the present invention is explained above. However, the present invention may be implemented in various different embodiments other than the embodiment described above within a technical scope described in claims.

All the automatic processes explained in the present embodiment can be, entirely or partially, carried out manually. Similarly, all the manual processes explained in the present embodiment can be, entirely or partially, carried out automatically by a known method.

The process procedures, the control procedures, specific names, information including registration data for each process and various parameters such as search conditions, display example, and database construction, mentioned in the description and drawings can be changed as required unless otherwise specified.

The constituent elements of the network model integration system 10, the network model integration device 100, the terminal device 130, and the external device 150 are merely conceptual and may not necessarily physically resemble the structures shown in the drawings.

For example, the process functions performed by each device of the network model integration device 100, the terminal device 130, and the external device 150, especially the each process function performed by the control unit 102, can be entirely or partially realized by CPU and a computer program executed by the CPU or by a hardware using wired logic. The computer program, recorded on a non-transitory computer readable recording medium including programmed commands for causing a computer to execute the method of the present invention, can be mechanically read by the network model integration device 100, the terminal device 130, and the external device 150 as the situation demands. In other words, the storage unit 106 such as read-only memory (ROM), SSD or HDD stores the computer program that can work in coordination with an operating system (OS) to issue commands to the CPU and cause the CPU to perform various processes. The computer program is first loaded to the random access memory (RAM), and forms the control unit in collaboration with the CPU.

Alternatively, the computer program can be stored in any application program server connected to the network model integration device 100, the terminal device 130, and the external device 150 via the network (communication line) 300, and can be fully or partially loaded as the situation demands.

The computer program may be stored in a computer-readable recording medium, or may be structured as a program product. Here, the "recording medium" includes any "portable physical medium" such as a memory card, a USB (Universal Serial Bus) memory, an SD (Secure Digital) card, a flexible disk, an optical disk, a ROM, an EPROM (Erasable Programmable Read Only Memory), an EEPROM (Electronically Erasable and Programmable Read Only Memory), a CD-ROM (Compact Disk Read Only Memory), an MO (Magneto-Optical disk), a DVD (Digital Versatile Disk), and a Blu-ray Disc.

In addition, a "program" is a data processing method that is described in an arbitrary language or a description method and may have an arbitrary form such as a source code, a binary code, or the like. Furthermore, the "program" is not necessarily limited to a configuration of a single form and includes a configuration in which the program is configured by a plurality of modules or a plurality of program libraries in a distributed manner and includes a program that achieves the function thereof in cooperation with a separate program that is represented by an OS. In addition, as a specific configuration for reading data from a recording medium in each apparatus illustrated in the embodiments, a reading procedure, an installation procedure after the reading, and the like, a known configuration and a known procedure may be used.

Various databases (the network model database 106a, the interaction database 106b, the pathway database 106c, the literature information database 106d, the news database 106e, the text mining database 106f, and the advertisement information database 106g) stored in the storage unit 106 is a storage unit such as a memory device such as a RAM or a ROM, a fixed disk device such as a HDD, a flexible disk, and an optical disk, and stores therein various programs, tables, databases, and web page files used for providing various processing or web sites.

The network model integration device 100, the terminal device 130, and the external device 150 may be structured as an information processing apparatus such as known personal computers or workstations, or may be structured by connecting any peripheral devices to the information processing apparatus. Furthermore, the network model integration device 100, the terminal device 130, and the external device 150 may be realized by mounting software (including programs, data, or the like) for causing the information processing apparatus to implement the method according of the invention.

The distribution and integration of the device are not limited to those illustrated in the figures. The device as a whole or in parts can be functionally or physically distributed or integrated in an arbitrary unit according to various attachments or how the device is to be used. That is, any embodiments described above can be combined when implemented, or the embodiments can selectively be implemented.

CONCLUSION OF PRESENT EMBODIMENT

As explained above, according to the present embodiment, it is possible to generate a series of retrieval instructions that are related to elements of a network model based on the network model designated by the user (the network model is a model that includes at least one constituent element, which may be registered in advance in the network model database 106a, may be newly registered in the network model database 106a by the user, and may be presented by the user via the terminal device 130 or a web service). According to the present embodiment, information on a series of interactions and constituent elements can be obtained from the interaction database 106b, a text mining device which is the external device 150 connected to the network model integration device 100, a pathway database, literature related databases possessed by publishers or the like, and various information sources on the Internet according to the retrieval instruction. According to the present embodiment, the network model designated by the user can be expanded by integrating the information into the network model designated by the user by presenting the information to the user to allow the user to select items within the information or automatically integrating the information based on certain criteria. In this case, in the present embodiment, it is possible to provide display mechanisms (that is, an arbitration function) to the constituent elements of the newly integrated interactions so that the user can identify the information sources or the like of the retrieval results that serve as the basis for presenting the items.

According to the present embodiment, when the user adds new information, expands the network model, or adds comments to the network model that is registered in the network model database 106a, the items of information can be provided to the person who has registered the network model. Further, in the present embodiment, the information added by the user can be provided to the person who has registered the network model by a method of displaying the information in such a form that the information can be clearly identified on the network model registered in advance and registering the same in an email or a designated database in a list form or the like. Furthermore, in the present embodiment, the person who has registered the network model can register the network model in which these items of information are added as a revision of the existing network model by selecting a portion or all of the items of information on a screen or the like.

According to the present embodiment, information on the interactions and constituent elements included in the network model that is registered or presented by the user can be extracted from the network model database 106a, and these items of information can be added to the interaction database 106b. Further, in the present embodiment, when the user expands the network model, the user can add evaluations on the information on the interactions and constituent elements that are presented as the retrieval results. Furthermore, in the present embodiment, by adding the retrieval results for the respective interactions and constituent elements to the interaction database 106b, it is possible to expand the interaction database and to accept evaluation information on the respective interactions and constituent elements.

According to the present embodiment, a retrieval instruction can be generated according to conditions (every 24 hours, every 48 hours, or the like) designated by the user in relation to the network model, the interaction, the constituent element, and the like designated by the user, and the retrieval results that meet the conditions (the retrieval results may be papers and related news and various announcements newly issued within the past 24 hours and may be related to the designated interaction, constituent element, and the like) can be presented to the user on the network model designated by the user or a list form or the like. Further, in the present embodiment, these retrieval results can be sent to an email address or the like designated by the user according to the instruction of the user.

According to the present embodiment, information providers (publishers, test reagent vendors, and the like) can provide information (advertisements) designated by the information providers to a user who has retrieved a partial structure or the like of a network model designated in advance by displaying the same on the display screen of the network model in a predetermined form or by sending the same to a registered mail address or the like of the user.

According to the present embodiment, a text mining, a natural language analysis method, or the like can be performed on a paper presented as retrieval results, and interactions or the like explained in the paper can be displayed in a machine-readable form or a graphical form. Further, in the present embodiment, by storing the information on the interactions in the interaction database 106b or the like, it is possible to establish associations between the respective interactions with literatures and to allow the users to easily understand which interaction and constituent element are covered by the literatures presented as the retrieval results.

Furthermore, in the present embodiment, the information on the interactions generated herein can be registered in the network model database 106a as a network model.

INDUSTRIAL APPLICABILITY

As explained above, according to the present invention, it is possible to provide a network model integration device, a network model integration system, a network model integration method, and a computer program product capable of displaying a network model of information related to biology such as an intermolecular interaction network, a transcription control network, an intercellular communication, or an interorgan interaction and expanding the network model based on a user's selection. Thus, the present invention is very useful in various fields such as medical, pharmaceutical, drug discovery, and biological research fields.

EXPLANATIONS OF LETTERS OR NUMERALS 10 network model integration system
100 network model integration device
102 control unit
102a retrieving unit
102b retrieval result displaying unit
102c integrating unit
102d network model storing unit
102e configuration notifying unit
102f note storing unit
102g note notifying unit
102h evaluation value storing unit
102i keyword acquiring unit
102j literature information retrieving unit
102k literature information displaying unit
102m literature information notifying unit
102n advertisement information acquiring unit
102p advertisement information displaying unit
102q network model displaying unit
102r literature model acquiring unit
106 storage unit
106a network model database
106b interaction database
106c pathway database
106d literature information database
106e news database
106f text mining database
106g advertisement information database
108 input/output control interface unit
112 input unit
114 display unit
130 terminal device
150 external device
300 network

The invention claimed is:

1. A network model integration device comprising:
an input unit;
a display unit;
a storage unit; and
a control unit, wherein
the storage unit includes:
a network model storage unit that stores a network model that includes nodes that represent constituent elements of a biological object and edges that represent interactions between the constituent elements and a network model ID that identifies the network model in association, and the control unit includes:
a retrieving unit that, when the network model is designated by a user via the input unit, retrieves the edges that are stored in the network model storage unit, do not constitute a designated network model which is the network model, and are linked to the nodes that constitute the designated network model,
a retrieval result displaying unit that displays retrieval results including the edges retrieved by the retrieving unit and the network model ID that identifies the network model including the edges stored in the network model storage unit on the display unit in a selectable manner,
an integrating unit that, when the retrieval results displayed on the display unit by the retrieval result displaying unit are selected by the user via the input unit, generates an integrated network model which is the network model in which the edges included in the selected retrieval results and the nodes that do not constitute the designated network model and are linked to the edges are integrated into the designated network model,
a network model storing unit that acquires the network model ID that identifies the integrated network model generated by the integrating unit and stores the integrated network model and the network model ID in the network model storage unit in association, and
a keyword acquiring unit that, when a portion or all of the network models, the nodes, or the edges are selected by the user via the input unit, acquires keywords related to the portion or all of the network models, the nodes, or the edges.

2. The network model integration device according to claim 1, wherein
the designated network model is the network model stored in the network model storage unit, an existing network model that is not stored in the network model storage unit, or a new network model.

3. The network model integration device according to claim 2, wherein
when the existing network model or the new network model is input by the user via the input unit, the network model storing unit further acquires the network model ID that identifies the designated network model and stores the designated network model and the network model ID in the network model storage unit in association.

4. The network model integration device according to claim 1,
wherein
when an ID selection instruction is input by the user via the input unit, the network model storing unit acquires the network model ID that identifies the designated network model, included in the integrated network model or a new network model ID as a network model ID that identifies the integrated network model based on the ID selection instruction and stores the integrated network model and the network model ID in the network model storage unit in association.

5. The network model integration device according to claim 1,
wherein
the storage unit further includes:
a pathway storage unit that stores pathways of the constituent elements;
a literature information storage unit that stores literature information on literatures related to the constituent elements and the interactions;

a news storage unit that stores news provided by a news delivery service; and a text mining storage unit that stores text information on the constituent elements and the interactions that are extracted from the literature information using text mining, the retrieving unit further retrieves the edges that do not constitute the designated network model and are linked to the nodes that constitute the designated network model from any one or all of the pathways stored in the pathway storage unit, the literature information stored in the literature information storage unit, the news stored in the news storage unit, and the text information stored in the text mining storage unit and acquires the network model ID that identifies the network model that includes the edges.

6. The network model integration device according to claim 1, wherein the retrieving unit retrieves the edges that are designated in advance by the user via the input unit.

7. The network model integration device according to claim 1, wherein the retrieval result displaying unit further displays the retrieval results including the nodes that do not constitute the designated network model and are linked to the edges retrieved by the retrieving unit and the network model ID that identifies the network model that includes the nodes stored in the network model storage unit on the display unit in a selectable manner.

8. The network model integration device according to claim 1, wherein the retrieval result displaying unit performs any one or both of a process of displaying the retrieval results on the display unit in a selectable manner in a list form and a process of displaying the retrieval results on the display unit so as to be superimposed on the network model.

9. The network model integration device according to claim 1, wherein the control unit further includes:

a configuration notifying unit that, when the edges stored in the network model storage unit are retrieved by the retrieving unit, notifies the user, who has provided the network model, of any one or both of the nodes and edges that are included in the designated network model and are not included in the network model stored in the network model storage unit, identified by the network model ID corresponding to the edges.

10. The network model integration device according to claim 1, wherein the control unit further includes:

a configuration notifying unit that, when the integrated network model is generated by the integrating unit, notifies the user, who has provided, the network model, of any one or both of the nodes and edges that are included in the integrated network model and are not included in the network model stored in the network model storage unit, identified by the network model ID corresponding to the edges that are included in the retrieval results that are selected by the user via the input unit.

11. The network model integration device according to claim 1, wherein the network model storage unit further stores notes for a portion or all of the network models, the nodes, or the edges in association with the portion or all of the network models, the nodes, or the edges, and the control unit further includes:

a note storing unit that, when the notes are input by the user via the input unit with respect to the portion or all of the network models, the nodes included in the network model, or the edges included in the network model, stored in the network model storage unit, stores the notes in the network model storage unit in association with the portion or all of the network models, the nodes, or the edges; and a note notifying unit that notifies the user, who has provided the network model corresponding to the notes, the network model that includes the nodes corresponding to the notes, or the network model that includes the edges corresponding to the notes, stored in the network model storage unit, of the notes stored in the network model storage unit.

12. The network model integration device according to claim 1, wherein the network model storage unit further stores evaluation values on the retrieval results in association with the edges included in the retrieval results, and the control unit further includes:

an evaluation value storing unit that, when evaluation values on the retrieval results are input by the user via the input unit, stores the evaluation values in the network model storage unit in association with the edges included in the retrieval results.

13. The network model integration device according to claim 12, wherein the evaluation values are input when the retrieval results displayed on the display unit by the retrieval result displaying unit are selected.

14. The network model integration device according to claim 12, wherein the retrieval result displaying unit further displays the evaluation values that are stored in the network model storage unit and correspond to the edges retrieved by the retrieving unit on the display unit.

15. The network model integration device according to claim 5, wherein the control unit further includes:

a literature information retrieving unit that retrieves the literature information on the literatures that are issued within a predetermined period and are stored in the literature information storage unit using the keywords acquired by the keyword acquiring unit at intervals that are set by the user via the input unit; and a literature information displaying unit that performs any one or both of a process of displaying the literature information retrieved by the literature information retrieving unit on the display unit in a list form and a process of displaying the literature information on the display unit so as to be superimposed on the network model stored in the network model storage unit.

16. The network model integration device according to claim 15, wherein
the control unit further includes:
a literature information notifying unit that notifies the user of the literature information retrieved by the literature information retrieving unit.

17. The network model integration device according to claim 15, wherein
the literature information displaying unit performs any one or both of the process of displaying the literature information on the display unit in the list form and the process of displaying the literature information on the display unit so as to be superimposed on the network model based on display preference conditions that are set by the user via the input unit.

18. The network model integration device according to claim 17, wherein
the display preference conditions are literature names, literature issuing organization names, or book titles.

19. The network model integration device according to claim 1,
wherein
the storage unit further includes:
an advertisement information storage unit that stores advertisement information on the constituent elements or the interactions, and
the control unit further includes:
an advertisement information acquiring unit that, when a portion or all of the network models, the nodes, or the edges are selected by the user via the input unit, acquires the advertisement information that is stored in the advertisement information storage unit and is related to the constituent elements or the interactions that are based on the portion or all of the network models, the nodes, or the edges; and
an advertisement information displaying unit that displays the advertisement information acquired by the advertisement information acquiring unit on the display unit.

20. The network model integration device according to claim 19, wherein
the advertisement information acquiring unit further acquires the advertisement information that is stored in the advertisement information storage unit and is related to neighboring constituent elements that interact with the constituent elements that are based on the portion or all of the network models, the nodes, or the edges.

21. The network model integration device according to claim 1, wherein
the storage unit further includes:
an advertisement information storage unit that stores advertisement information related to the constituent elements or the interactions, and
the control unit further includes:
a network model displaying unit that displays the network model on the display unit;
an advertisement information acquiring unit that recognizes a portion of the network model that is displayed at a center of a screen for the longest period within a predetermined period by the network model displaying unit and acquires the advertisement information that is stored in the advertisement information storage unit and is related to any one or both of the constituent elements based on the nodes and the interactions based on the edges, included in the portion of the network model; and
an advertisement information displaying unit that displays the advertisement information acquired by the advertisement information acquiring unit on the display unit.

22. The network model integration device according to claim 5, wherein
the control unit further includes:
a literature model acquiring unit that acquires the network model from the literature information in which the edges are retrieved by the retrieving unit using natural language analysis and acquires a network model ID that identifies the network model, and
the network model storing unit further stores the network model acquired by the literature model acquiring unit and the network model ID in the network model storage unit in association.

23. A network model integration system comprising:
a network model integration device including a control unit and a storage unit; and
a terminal device including an input unit, a display unit, and a control unit, the network model integration device and the terminal device being that are connected to each other in a communicable manner, wherein
the storage unit of the network model integration device includes:
a network model storage unit that stores a network model that includes nodes that represent constituent elements of a biological object and edges that represent interactions between the constituent elements and a network model ID that identifies the network model in association,
the control unit of the network model integration device includes:
a retrieving unit that retrieves the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device,
an integrating unit that generates an integrated network model which is the network model in which the edges included in the retrieval results that are transmitted from the terminal device and are selected by the user via the input unit and the nodes that do not constitute the designated network model and are linked to the edges are integrated into the designated network model,
a network model storing unit that acquires the network model ID that identifies the integrated network model generated by the integrating unit and stores the integrated network model and the network model ID in the network model storage unit in association, and
a keyword acquiring unit that, when a portion or all of the network models, the nodes, or the edges are selected by the user via the input unit, acquires keywords related to the portion or all of the network models, the nodes, or the edges, and
the control unit of the terminal device includes:
a retrieval result displaying unit that displays the retrieval results transmitted from the network model integration device on the display unit in a selectable manner and transmits the retrieval results selected by the user via the input unit to the terminal device.

24. A network model integration method executed by a network model integration device including an input unit, a display unit, a storage unit, and a control unit, wherein
the storage unit includes:
a network model storage unit that stores a network model that includes nodes that represent constituent elements of a biological object and edges that represent interactions between the constituent elements and a network model ID that identifies the network model in association,
the method executed by the control unit comprising:
a retrieving step of retrieving the edges that are stored in the network model storage unit, do not constitute a designated network model which is the network model, and are linked to the nodes that constitute the designated network model, when the network model is designated by a user via the input unit;
a retrieval result displaying step of displaying retrieval results including the edges retrieved at the retrieving step and the network model ID that identifies the network model including the edges stored in the network model storage unit on the display unit in a selectable manner;
an integrating step of generating an integrated network model which is the network model in which the edges included in the selected retrieval results and the nodes that do not constitute the designated network model and are linked to the edges are integrated into the designated network model, when the retrieval results displayed on the display unit at the retrieval result displaying step are selected by the user via the input unit;
a network model storing step of acquiring the network model ID that identifies the integrated network model generated at the integrating step and storing the integrated network model and the network model ID in the network model storage unit in association; and
a keyword acquiring step of, when a portion or all of the network models, the nodes, or the edges are selected by the user via the input unit, acquiring keywords related to the portion or all of the network models, the nodes, or the edges.

25. A network model integration method that is performed in a network model integration system including a network model integration device including a control unit and a storage unit and a terminal device including an input unit, a display unit, and a control unit that are connected to each other in a communicable manner, wherein
the storage unit of the network model integration device includes:
a network model storage unit that stores a network model that includes nodes that represent constituent elements of a biological object and edges that represent interactions between the constituent elements and a network model ID that identifies the network model in association,
the method comprising:
a retrieving step of retrieving the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device that is performed by the control unit of the network model integration device;
a retrieval result displaying step of displaying the retrieval results transmitted from the network model integration device on the display unit in a selectable manner and transmits the retrieval results selected by the user via the input unit to the terminal device that is performed by the control unit of the terminal apparatus;
an integrating step of generates an integrated network model which is the network model in which the edges included in the retrieval results that are transmitted from the terminal device and are selected by the user via the input unit and the nodes that do not constitute the designated network model and are linked to the edges are integrated into the designated network model that is performed by the control unit of the network model integration device;
a network model storing step of acquires the network model ID that identifies the integrated network model generated at the integrating step and storing the integrated network model and the network model ID in the network model storage unit in association that is performed by the control unit of the network model integration device; and
a keyword acquiring step of, when a portion or all of the network models, the nodes, or the edges are selected by the user via the input unit, acquiring keywords related to the portion or all of the network models, the nodes, or the edges.

26. A computer program product having a non-transitory computer readable medium including programmed instructions for a network model integration method executed by a network model integration device including an input unit, a display unit, a storage unit, and a control unit, wherein
the storage unit includes:
a network model storage unit that stores a network model that includes nodes that represent constituent elements of a biological object and edges that represent interactions between the constituent elements and a network model ID that identifies the network model in association, wherein
the instructions, when executed by the control unit, cause the control unit to execute:
a retrieving step of retrieving the edges that are stored in the network model storage unit, do not constitute a designated network model which is the network model, and are linked to the nodes that constitute the designated network model, when the network model is designated by a user via the input unit;
a retrieval result displaying step of displaying retrieval results including the edges retrieved at the retrieving step and the network model ID that identifies the network model including the edges stored in the network model storage unit on the display unit in a selectable manner;
an integrating step of generating an integrated network model which is the network model in which the edges included in the selected retrieval results and the nodes that do not constitute the designated network model and are linked to the edges are integrated into the designated network model, when the retrieval results displayed on the display unit at the retrieval result displaying step are selected by the user via the input unit;
a network model storing step of acquiring the network model ID that identifies the integrated network model generated at the integrating step and stores the integrated network model and the network model ID in the network model storage unit in association; and a keyword acquiring step of, when a portion or all of the network models, the nodes, or the edges are selected by the user via the input unit, acquiring keywords related to the portion or all of the network models, the nodes, or the edges.

27. A computer program product having a non-transitory computer readable medium including programmed instructions for a network model integration method executed by a network model integration device including a control unit and a storage unit that is connected to a terminal device including an input unit in a communicable manner, wherein the storage unit includes:
a network model storage unit that stores a network model that includes nodes that represent constituent elements of a biological object and edges that represent interactions between the constituent elements and a network model ID that identifies the network model in association, wherein the instructions, when executed by the control unit, cause the control unit to execute:

a retrieving step of retrieving the edges that are stored in the network model storage unit, do not constitute a designated network model which is the network model that is transmitted from the terminal device and is designated by a user of the terminal device via the input unit, and are linked to the nodes that constitute the designated network model and transmits retrieval results including the retrieved edges and the network model ID that identifies the network model that includes the edges stored in the network model storage unit to the terminal device;

an integrating step of generates an integrated network model which is the network model in which the edges included in the retrieval results that are transmitted from the terminal device and are selected by the user via the input unit and the nodes that do not constitute the designated network model and are linked to the edges are integrated into the designated network model;

a network model storing step of acquires the network model ID that identifies the integrated network model generated at the integrating step and stores the integrated network model and the network model ID in the network model storage unit in association; and a keyword acquiring step of, when a portion or all of the network models, the nodes, or the edges are selected by the user via the input unit, acquiring keywords related to the portion or all of the network models, the nodes, or the edges.

* * * * *